United States Patent
Chuang et al.

(10) Patent No.: US 8,812,071 B2
(45) Date of Patent: Aug. 19, 2014

(54) TRANSDERMAL ANALYTE MONITORING SYSTEMS AND METHODS FOR ANALYTE DETECTION

(75) Inventors: Han Chuang, Canton, MA (US); James P. Hurley, Canton, MA (US); Joseph Kost, Omer (IL)

(73) Assignee: Echo Therapeutics, Inc., Philadelphia, PA (US)

( * ) Notice: Subject to any disclaimer, the term of this patent is extended or adjusted under 35 U.S.C. 154(b) by 346 days.

(21) Appl. No.: 12/043,469

(22) Filed: Mar. 6, 2008

(65) Prior Publication Data

US 2008/0281178 A1 Nov. 13, 2008

Related U.S. Application Data

(60) Provisional application No. 60/893,563, filed on Mar. 7, 2007.

(51) Int. Cl.
| | |
|---|---|
| *A61B 5/05* | (2006.01) |
| *A61B 5/00* | (2006.01) |
| *A61B 5/145* | (2006.01) |
| *A61B 5/1486* | (2006.01) |

(52) U.S. Cl.
CPC ............ *A61B 5/0002* (2013.01); *A61B 5/6833* (2013.01); *A61B 5/14546* (2013.01); *A61B 5/1486* (2013.01); *A61B 5/14532* (2013.01)
USPC ............................ 600/345; 600/347; 600/365

(58) Field of Classification Search
USPC .................................. 600/316, 345–348, 365
See application file for complete search history.

(56) References Cited

U.S. PATENT DOCUMENTS

| | | | |
|---|---|---|---|
| 3,551,554 | A | 12/1970 | Herschler |
| 3,711,602 | A | 1/1973 | Herschler |
| 3,711,606 | A | 1/1973 | Herschler |

(Continued)

FOREIGN PATENT DOCUMENTS

| | | |
|---|---|---|
| CA | 2196746 | 8/1991 |
| CA | 1324051 | 11/1993 |

(Continued)

OTHER PUBLICATIONS

Agrawal, et al., "The effects of ultrasound irradiation on a biodegradable 50-50% copolymer of polylactic and polyglycolic acids", *J Biomed Mater Res.*, 28(8):851-9 (1994).

(Continued)

*Primary Examiner* — Michael D'Angelo
(74) *Attorney, Agent, or Firm* — Pabst Patent Group LLP

(57) ABSTRACT

Transdermal analyte monitoring systems (TAMS) having increased longevity and improved analyte detection are described herein. Kits for use with the TAMS and methods of using the TAMS and kits are also described. In a preferred embodiment, the TAMS includes a protective, semi-permeable membrane covering the surface of the hydrogel. The protective, semi-permeable membrane contacts with the skin of a user and prevents contamination or fouling of the hydrogel. Optionally, the hydrogel comprises one or more humectants and/or an immobilized enzyme. In another preferred embodiment, the TAMS contains at least one channel or pocket for increasing the amount of oxygen provided to the hydrogel. In one embodiment, a method for improving analyte detection by the TAMS is provided. For example, after the skin porosity is increased by an appropriate pretreatment, a skin preparation wipe is applied to the treated skin area and then the TAMS is applied to the treated area.

16 Claims, 12 Drawing Sheets

(56) References Cited

U.S. PATENT DOCUMENTS

| | | | |
|---|---|---|---|
| 3,828,769 | A | 8/1974 | Metler |
| 4,002,221 | A | 1/1977 | Buchalter |
| 4,020,830 | A | 5/1977 | Johnson et al. |
| 4,127,125 | A | 11/1978 | Takemoto et al. |
| 4,144,646 | A | 3/1979 | Takemoto et al. |
| 4,176,664 | A | 12/1979 | Kalish |
| 4,249,531 | A | 2/1981 | Heller et al. |
| 4,280,494 | A | 7/1981 | Cosgrove, Jr. et al. |
| 4,309,989 | A | 1/1982 | Fahim |
| 4,372,296 | A | 2/1983 | Fahim |
| 4,457,748 | A | 7/1984 | Lattin et al. |
| 4,537,776 | A | 8/1985 | Cooper |
| 4,557,943 | A | 12/1985 | Rosler et al. |
| 4,563,184 | A | 1/1986 | Korol |
| 4,595,011 | A | 6/1986 | Phillips |
| 4,605,670 | A | 8/1986 | Saito et al. |
| 4,646,725 | A | 3/1987 | Moasser |
| 4,657,543 | A | 4/1987 | Langer et al. |
| 4,683,242 | A | 7/1987 | Poser |
| 4,698,058 | A | 10/1987 | Greenfeld et al. |
| 4,721,677 | A | 1/1988 | Clark, Jr. |
| 4,732,153 | A | 3/1988 | Phillips |
| 4,767,402 | A | 8/1988 | Kost et al. |
| 4,779,806 | A | 10/1988 | Langer et al. |
| 4,780,212 | A | 10/1988 | Kost et al. |
| 4,786,277 | A | 11/1988 | Power et al. |
| 4,787,070 | A | 11/1988 | Suzuki et al. |
| 4,787,888 | A | 11/1988 | Fox |
| 4,805,623 | A | 2/1989 | Jobsis |
| 4,820,720 | A | 4/1989 | Sanders et al. |
| 4,821,733 | A | 4/1989 | Peck |
| 4,821,740 | A | 4/1989 | Tachibana et al. |
| 4,834,978 | A | 5/1989 | Nuwayser |
| 4,855,298 | A | 8/1989 | Yamada et al. |
| 4,860,058 | A | 8/1989 | Kobayashi et al. |
| 4,863,970 | A | 9/1989 | Patel et al. |
| 4,866,050 | A | 9/1989 | Ben-Amoz |
| 4,933,062 | A | 6/1990 | Shaw et al. |
| 4,948,587 | A | 8/1990 | Kost et al. |
| 4,953,552 | A | 9/1990 | DeMarzo |
| 4,953,565 | A | 9/1990 | Tachibana et al. |
| 4,970,145 | A | 11/1990 | Bennetto et al. |
| 4,981,779 | A | 1/1991 | Wagner |
| 4,986,271 | A | 1/1991 | Wilkins |
| 5,001,051 | A | 3/1991 | Miller et al. |
| 5,006,342 | A | 4/1991 | Cleary et al. |
| 5,007,438 | A | 4/1991 | Tachibana et al. |
| 5,008,110 | A | 4/1991 | Benecke et al. |
| 5,016,615 | A | 5/1991 | Driller et al. |
| 5,019,034 | A | 5/1991 | Weaver et al. |
| 5,050,604 | A | 9/1991 | Reshef et al. |
| 5,069,908 | A | 12/1991 | Henley |
| 5,076,273 | A | 12/1991 | Schoendorfer et al. |
| 5,078,144 | A | 1/1992 | Sekino et al. |
| 5,082,786 | A | 1/1992 | Nakamoto |
| 5,086,229 | A | 2/1992 | Rosenthal et al. |
| 5,115,805 | A | 5/1992 | Bommannan et al. |
| 5,118,404 | A | 6/1992 | Saito |
| 5,119,819 | A | 6/1992 | Thomas et al. |
| 5,120,544 | A | 6/1992 | Henley |
| 5,134,057 | A | 7/1992 | Kuypers et al. |
| 5,135,753 | A | 8/1992 | Baker et al. |
| 5,139,023 | A | 8/1992 | Stanley et al. |
| 5,140,985 | A | 8/1992 | Schroeder et al. |
| 5,161,532 | A | 11/1992 | Joseph |
| 5,165,407 | A | 11/1992 | Wilson et al. |
| 5,165,418 | A | 11/1992 | Tankovich |
| 5,171,215 | A | 12/1992 | Flanagan |
| 5,197,946 | A | 3/1993 | Tachibana |
| 5,215,520 | A | 6/1993 | Shroot et al. |
| 5,215,887 | A | 6/1993 | Saito |
| 5,230,334 | A | 7/1993 | Klopotek |
| 5,231,975 | A | 8/1993 | Bommannan et al. |
| 5,236,410 | A | 8/1993 | Granov et al. |
| 5,250,419 | A | 10/1993 | Bernard et al. |
| 5,267,985 | A | 12/1993 | Shimada et al. |
| 5,279,543 | A | 1/1994 | Glikfeld et al. |
| 5,282,785 | A | 2/1994 | Shapland et al. |
| 5,286,254 | A | 2/1994 | Shapland et al. |
| 5,315,998 | A | 5/1994 | Tachibana et al. |
| 5,323,769 | A | 6/1994 | Bommannan et al. |
| 5,330,756 | A | 7/1994 | Steuart et al. |
| 5,364,838 | A | 11/1994 | Rubsamen |
| 5,386,837 | A | 2/1995 | Sterzer |
| 5,401,237 | A | 3/1995 | Tachibana et al. |
| 5,405,366 | A * | 4/1995 | Fox et al. .................. 607/50 |
| 5,405,614 | A | 4/1995 | D'Angelo et al. |
| 5,413,550 | A | 5/1995 | Castel |
| 5,415,629 | A | 5/1995 | Henley |
| 5,421,816 | A | 6/1995 | Lipkovker |
| 5,421,982 | A | 6/1995 | Ikeda |
| 5,429,735 | A | 7/1995 | Johnson et al. |
| 5,443,080 | A | 8/1995 | D'Angelo et al. |
| 5,445,611 | A | 8/1995 | Eppstein et al. |
| 5,458,140 | A | 10/1995 | Eppstein et al. |
| 5,470,582 | A | 11/1995 | Supersaxo et al. |
| 5,482,927 | A | 1/1996 | Maniar et al. |
| 5,534,496 | A | 7/1996 | Lee et al. |
| 5,538,503 | A | 7/1996 | Henley |
| 5,569,198 | A | 10/1996 | Racchini |
| 5,573,778 | A | 11/1996 | Therriault et al. |
| 5,581,438 | A | 12/1996 | Halliop |
| 5,582,184 | A | 12/1996 | Erickson et al. |
| 5,582,586 | A | 12/1996 | Tachibana et al. |
| 5,617,851 | A | 4/1997 | Lipkovker |
| 5,618,275 | A | 4/1997 | Bock |
| 5,626,554 | A | 5/1997 | Ryaby et al. |
| 5,632,307 | A | 5/1997 | Fawley et al. |
| 5,636,632 | A | 6/1997 | Bommannan et al. |
| 5,646,221 | A | 7/1997 | Inag et al. |
| 5,655,539 | A | 8/1997 | Wang et al. |
| 5,656,016 | A | 8/1997 | Ogden |
| 5,658,247 | A | 8/1997 | Henley |
| 5,667,487 | A | 9/1997 | Henley |
| 5,722,397 | A | 3/1998 | Eppstein |
| 5,730,714 | A | 3/1998 | Guy et al. |
| 5,735,273 | A | 4/1998 | Kurnik et al. |
| 5,746,217 | A | 5/1998 | Erickson et al. |
| 5,771,890 | A | 6/1998 | Tamada |
| 5,782,754 | A | 7/1998 | Korf et al. |
| 5,814,599 | A | 9/1998 | Mitragotri et al. |
| 5,820,570 | A | 10/1998 | Erickson et al. |
| 5,827,183 | A | 10/1998 | Kurnik et al. |
| 5,833,647 | A | 11/1998 | Edwards |
| 5,885,211 | A | 3/1999 | Eppstein et al. |
| 5,895,362 | A | 4/1999 | Elstrom et al. |
| 5,902,603 | A | 5/1999 | Chen et al. |
| 5,906,830 | A | 5/1999 | Farinas et al. |
| 5,913,833 | A | 6/1999 | Elstrom et al. |
| 5,919,835 | A | 7/1999 | Domb et al. |
| 5,947,921 | A | 9/1999 | Johnson et al. |
| 5,961,451 | A | 10/1999 | Reber et al. |
| 5,989,409 | A | 11/1999 | Kurnik et al. |
| 6,002,961 | A | 12/1999 | Mitragotri et al. |
| 6,002,962 | A | 12/1999 | Huang et al. |
| 6,009,343 | A | 12/1999 | Shain et al. |
| 6,018,678 | A | 1/2000 | Mitragotri et al. |
| 6,041,253 | A | 3/2000 | Kost et al. |
| 6,139,718 | A | 10/2000 | Kurnik et al. |
| 6,190,315 | B1 | 2/2001 | Kost et al. |
| 6,212,416 | B1 | 4/2001 | Ward et al. |
| 6,233,471 | B1 | 5/2001 | Berner et al. |
| 6,234,990 | B1 | 5/2001 | Rowe et al. |
| 6,251,083 | B1 | 6/2001 | Yum et al. |
| 6,283,926 | B1 | 9/2001 | Cunningham et al. |
| 6,287,438 | B1 | 9/2001 | Knoll |
| 6,299,578 | B1 | 10/2001 | Kurnik et al. |
| 6,309,351 | B1 | 10/2001 | Kurnik et al. |
| 6,309,535 | B1 | 10/2001 | Williams et al. |
| 6,468,229 | B1 | 10/2002 | Grace et al. |
| 6,482,604 | B2 | 11/2002 | Kwon |
| 6,487,447 | B1 | 11/2002 | Weimann et al. |
| 6,491,657 | B2 | 12/2002 | Rowe et al. |
| 6,503,198 | B1 | 1/2003 | Aronowtiz et al. |

(56) References Cited

U.S. PATENT DOCUMENTS

| | | | |
|---|---|---|---|
| 6,535,753 B1 | 3/2003 | Raskas | |
| 6,540,675 B2 | 4/2003 | Aceti et al. | |
| 6,595,919 B2 | 7/2003 | Berner et al. | |
| 6,673,596 B1 | 1/2004 | Sayler et al. | |
| 6,766,817 B2 | 7/2004 | Da Silva | |
| 6,887,239 B2 | 5/2005 | Elstrom et al. | |
| 6,931,327 B2 | 8/2005 | Goode, Jr. et al. | |
| 7,108,778 B2 | 9/2006 | Simpson et al. | |
| 7,110,803 B2 | 9/2006 | Shults et al. | |
| 7,150,975 B2* | 12/2006 | Tamada et al. | 435/14 |
| 7,432,069 B2 | 10/2008 | Barman et al. | |
| 7,963,917 B2 | 6/2011 | Kellogg et al. | |
| 2001/0017269 A1 | 8/2001 | Heller et al. | |
| 2002/0058051 A1* | 5/2002 | Nawaz et al. | 424/401 |
| 2003/0027240 A1 | 2/2003 | Asher et al. | |
| 2003/0100040 A1 | 5/2003 | Bonnecaze et al. | |
| 2003/0100846 A1 | 5/2003 | Custer et al. | |
| 2003/0232895 A1 | 12/2003 | Omidian et al. | |
| 2004/0039418 A1 | 2/2004 | Elstrom et al. | |
| 2004/0087671 A1 | 5/2004 | Tamada et al. | |
| 2004/0167383 A1 | 8/2004 | Kim et al. | |
| 2004/0171980 A1 | 9/2004 | Mitragotri et al. | |
| 2004/0176672 A1 | 9/2004 | Silver et al. | |
| 2004/0236268 A1 | 11/2004 | Mitragotri et al. | |
| 2005/0027180 A1 | 2/2005 | Goode et al. | |
| 2006/0015058 A1 | 1/2006 | Kellogg et al. | |
| 2006/0094944 A1 | 5/2006 | Chuang | |
| 2006/0094945 A1 | 5/2006 | Barman et al. | |
| 2006/0094946 A1* | 5/2006 | Kellogg et al. | 600/347 |
| 2006/0195029 A1* | 8/2006 | Shults et al. | 600/345 |

FOREIGN PATENT DOCUMENTS

| | | |
|---|---|---|
| CA | 2226176 | 1/1997 |
| CA | 2212826 | 7/1997 |
| CA | 2075624 | 11/1997 |
| CA | 2196746 | 8/1999 |
| DE | 2756460 | 6/1979 |
| EP | 0043738 | 1/1982 |
| EP | 0 246 341 | 11/1987 |
| EP | 0245535 | 11/1987 |
| EP | 0247850 | 12/1987 |
| EP | 0278074 | 8/1988 |
| EP | 0304304 | 2/1989 |
| EP | 0368408 | 5/1990 |
| EP | 0 396 788 | 11/1990 |
| EP | 0453283 | 10/1991 |
| EP | 0 495 531 | 7/1992 |
| EP | 0 513 789 | 11/1992 |
| EP | 0588238 | 3/1994 |
| EP | 0 612 525 | 8/1994 |
| EP | 0625360 | 11/1994 |
| EP | 0 649 628 | 4/1995 |
| EP | 0 736 305 | 10/1996 |
| EP | 1266608 | 12/2002 |
| GB | 1 577 551 | 10/1980 |
| GB | 1577551 | 10/1980 |
| GB | 2153223 | 12/1984 |
| JP | 59-95060 | 5/1984 |
| JP | 62133937 | 6/1987 |
| JP | 3 170 172 | 7/1991 |
| JP | 2002162353 | 6/2002 |
| JP | 3366646 | 11/2002 |
| JP | 2002/542498 | 12/2002 |
| JP | 2003/527613 | 9/2003 |
| SU | 445433 | 11/1974 |
| SU | 556805 | 6/1977 |
| SU | 591186 | 1/1978 |
| SU | 506421 | 2/1978 |
| SU | 910157 | 3/1982 |
| WO | WO 87/07295 | 12/1987 |
| WO | WO 88/00001 | 1/1988 |
| WO | WO 90/01971 | 8/1990 |
| WO | WO 90/15568 | 12/1990 |
| WO | WO 91/12772 | 9/1991 |
| WO | WO 92/13567 | 8/1992 |
| WO | WO 92/14449 | 9/1992 |
| WO | WO 93/05096 | 3/1993 |
| WO | WO 93/20745 | 10/1993 |
| WO | WO 94/08655 | 4/1994 |
| WO | WO 94/05368 | 8/1994 |
| WO | WO 95/02357 | 1/1995 |
| WO | WO 96/00110 | 1/1996 |
| WO | WO 97/02811 | 1/1997 |
| WO | WO 97/04832 | 2/1997 |
| WO | WO 97/10356 | 3/1997 |
| WO | WO 97/10499 | 3/1997 |
| WO | WO 97/13548 | 4/1997 |
| WO | WO 97/18851 | 5/1997 |
| WO | WO 97/24059 | 7/1997 |
| WO | WO 97/30628 | 8/1997 |
| WO | WO 97/30749 | 8/1997 |
| WO | WO 98/00194 | 1/1998 |
| WO | WO 98/17184 | 4/1998 |
| WO | WO 98/20331 | 5/1998 |
| WO | WO 98/28037 | 7/1998 |
| WO | WO 98/34541 | 8/1998 |
| WO | WO 98/42252 | 10/1998 |
| WO | 9913336 | 3/1999 |
| WO | WO 99/34857 | 7/1999 |
| WO | WO 99/34858 | 7/1999 |
| WO | WO 99/39763 | 8/1999 |
| WO | WO 00/04821 | 2/2000 |
| WO | WO 00/09203 | 2/2000 |
| WO | WO 00/35351 | 6/2000 |
| WO | WO 00/35357 | 6/2000 |
| WO | 0065143 | 11/2000 |
| WO | WO 00/64533 | 11/2000 |
| WO | WO 01/70330 | 9/2001 |
| WO | 0245761 | 6/2002 |
| WO | 03056033 | 7/2003 |
| WO | 2004099777 | 11/2004 |
| WO | 2006007472 | 1/2006 |
| WO | 2006050032 | 5/2006 |
| WO | WO 2006/124759 | 11/2006 |

OTHER PUBLICATIONS

Albin, et al., "Theoretical and experimental studies of glucose sensitive membranes", *Journal of Controlled Release*, 6 (1):267-291, (1987).

Allcock, et al., "Activity of urea amidohydrolase immobilized within poly[di(methoxyethoxyethoxy)phosphazene] hydrogels", *Biomaterials*, 15(7):502-6 (1994).

Apfel, "Possibility of microcavitation from diagnostic ultrasound" *IEEE Trans. Ultrason Ferroelectrics Freq. Control UFFC*, 33:139-142 (1986).

Asakura, et al., "Immobilization of glucose oxidase on nonwoven fabrics with *Bombyx mori* silk fibroin gel" *J. Appl. Pol. Sci.*, 4(1): 49-53 (1992).

Aungst, et al., "Contributions of drug solubilization, partitioning, barrier disruption, and solvent permeation to the enhancement of skin permeation of various compounds with fatty acids and amines", *Pharm Res.*, 7(7):712-8 (1990).

Barry, et al., "Mode of Action of Penetration Enhancers in human skin", *J. Control. Rel.*, 6:85-97 (1987).

Bhat, et al., "Optimization of delivery of bethamethasone-dipropionate from skin preparation", *Indian Drugs*, 32:211-214 (1995).

Blackshear, "Implantable drug-delivery systems", *Scientific America*, 241(56):66-73 (1979).

Bommer et al., "Subcutaneous erythropoietin", *Lancet*, 2(8607):406 (1988).

Boucaud, et al., "Clinical, histologic, and electron microscopy study of skin exposed to low-frequency ultrasound", *Anat Rec.*, 264(1):114-9 (2001).

Boucaud, et al., "In vitro study of low-frequency ultrasound-enhanced transderml transport of fentanyl and caffeine across human and hairless rat skin", *Int J Pharm.*, 228(1-2):69-77 (2001).

(56) References Cited

OTHER PUBLICATIONS

Burnette, "Iontophoresis", in Transdermal Drug Delivery Development Issues and Research Initiatives p. 247-291 (Hadgraft and Guy, Eds. Marcel Dekker, 1989).

Burton, et al., "Metabolism and transport of peptide across intestinal mucosa" *Proceed. Intern. Symp. Control. Rel. Bioact. Mater*, 14: 6-7 (Controlled Release Society, Inc. 1987).

Camel, "Ultrasound" in Percutaneous Penetration Enhancers p. 369-382 (Eric W. Smith, et al. eds. 1995).

Chlup, et al., "Function and accuracy of glucose sensors beyond their stated expiry date", *Diabetes Technology & Therapeutics*, 8(4):495-504 (2005).

Chuang, et al., *"Ultrasonic Pretreatment Enables Continuous Transdermal Glucose Monitoring"*, A29, Presented at the 4th Annual Diabetes Technology Meeting Held Oct. 28-30, 2004, (Philadelphia, PA).

Cleary, "Transdermal Controlled Release Systems," in Medical Applications of Controlled Release, pp. 203-251 (Langer and Wise eds. CRC Press 1984).

Cleg and Vaz, "Translational diffusion of proteins and lipids in artificial lipid bilayer membranes, A comparison of experiment with theory", in Progress in Protein-Lipid Interactions Watts, ed. Chapter 5, pp. 173-339 (Elsevier, NY 1985).

Davis, et al., "Characterization of recombinant human erythropoietin produced in Chinese hamster ovary cells", *Biochemistry*, 26(9):2633-8 (1987).

D'Emanuele, et al., "An investigation of the effects of ultrasound on degradable polyanhydride matrices" *Macromols.*, 25:511-515 (1992).

Domb, et al., "Polyanhydrides-Synthesis and Characterization," *Advances in Polymer Science*, 107:93-141 (1993).

Ebert, et al., "Transbuccal Absorption of Diclofenac Sodium in a Dog Model," Controlled Release Technology Pharmaceutical Application, pp. 310-321 (Lee, et al. Editors, American Chemical Society, 1987).

Eggerth, et al; "Evaluation of Hamster Cheek Pouch as a Model for Buccal Absorption," *Proceed. Intern. Symp. Rel. Bioact. Mater.* 14:180-181 (Controlled Release Society, Inc. 1987).

Elias, The Microscopic Structure of the Epidermis and its Derivatives, Percutaneous Absorption: Mechanisms—Methodology—Drug Delivery, pp. 1-12 (1989).

Eppstein, et al; "Alternative Delivery Systems for Peptides and Proteins as Drugs," *Crit Rev Ther. Drug Carrier Syst.*, 5:99-139 (1988).

Eppstein, et al; Applications of Liposome Formulations for Antimicrobial/Antiviral Therapy, In: Liposomes as Drug Carriers, Gregoriadis G. eds. pp. 311-323, John Wiley & Sons, Chichester, 1988.

Eppstein, "Medical Utility of Interferons: Approaches to Increasing Therapeutic Efficacy", Pharmacy International 7:195-199 (1986).

Flynn, Mechanism of Percutaneous Absorption from Physicochemical Evidence, in: Bronaugh R. Maibach HI. Eds. Percutaneous Absorption: Mechanisms—Methodology—Drug Delivery, New York, NY, Marcel Dekker, pp. 27-51 (1989).

Gaertner, "Frequency dependence of Ultrasonic Cavitation," *J. Acoust. Soc. Am.* 26:977-980 (1954).

Ghanem, et al; "The effects of ethanol on the transport of lipophilic and polar permeants across hairless mouse skin: Methods/validation of a novel approach," *Int. J. Pharm.*, 78:137-156 (1992).

Grups and Frohmueller, "Cyclic Interferon Gamma Treatment of Patients with Metastatic Renal Carcinoma," *Br. J. Urol.*, 64(3):218-220(1989).

Heller, et al., "Controlled Drug Release by Polymer Dissolution II Enzyme-Mediated Delivery Device," *J. of Pharm. Sci.*, vol. 68(7):919-921 (1979).

Hill-West, et al., "Inhibition of thrombosis and intimal thickening by in situ photopolymerization of thin hydrogel barriers", *Proc Natl Acad Sci U S A*, 91:5967-71 (1994).

Johnson, et al., "Synergistic effects of chemical enhancers and therapeutic ultrasound on transdermal drug delivery," *J. Pharm. Sci.*, 85:670-679 (1996).

Junginger, et al., "Visualization of Drug Transportation Across Human Skin and the Influence of Penetration Enhancers," in: Drug Permeation Enhancement Hsieh, D.S., Editors, Marcel Dekker, Inc. New York (1994), pp. 59-89.

Kamath, et al; "Biodegradable hydrogels in Drug Delivery," *Adv. Drug Delivery Rev.*, 11:59-84 (1993).

Kasting, et al; "Prodrugs for Dermal Delivery: Solubility, molecular Size, and Functional Group Effects," in: Prodrugs: Topical and Ocular Delivery Sloan, ed. (Marcel Dekker, NY 1992) pp. 117-161.

Keith and Snipes, "Polymeric carriers for Active Agents," in: Transdermal and Related Drug Delivery Systems, pp. 223-279 (D. A. Jones ed. 1984).

Klonoff, "A review of continuous glucose monitoring technology", *Diabetes Technology & Therapeutics*, 7(5):770-775 (2005).

Kost and Langer, "Ultrasound-Mediated Transdermal Drug Delivery," in: Topical Drug Bioavailability Bioequivalence and Penetration (Maibach, H. I., Shah, V. P., Editors, Plenum Press, New York), pp. 91-104 (1993).

Kost, et al; "Ultrasound Effect on Transdermal Drug Delivery," Proceeding of the $13^{th}$ International Symposium on Controlled Release of Bioactive Materials, Norfolk, VA, 1986, pp. 177-178.

Kost, et al., "Glucose-Sensitive Membranes containing Glucose Oxidase: Activity, Swelling, and Permeability Studies," *J. of Biomed. Mat. Res.*, 19: 1117-1133 (1985).

Krall, "World Book of Diabetes in Practice," vol. 3, pp. 2-7 (Elsvier, 1988).

Langer, et al., "Chemical and Physical Structure of Polymers as Carriers for Controlled Release of Bioactive Agents: A Review," *J. of Macromol. Sci., Reviews on Macromolecular Chemistry and Physics*, C23(1):61-126 (1983).

Lee & Rashi, "Nasal Peptide and Protein Absorption Promoters: Aminopeptidase Inhibition as a Predictor of Absorption Enhancement Potency of Bile Salts," *Proc. Intern. Symp. Control. Rel. Bioact. Mater.*, 14:53-54 (1987).

Lee, et al., "Protease Inhibition as an Additional Mechanism for the Nasal Absorption Enhancement Effect of Sodium Taurodihydrofusidate," *Proceed. Intern. Symp. Control. Rel. Bioact. Mater.*, 14, 55-56 (1987).

Lesho, et al., "A Photopatterned Glucose Responsive Hydrogel for Use in a Conductimetric Sensor," in: Biomaterials for Drug and Cell Delivery, Materials Research Society Symposium Proceedings, vol. 331, pp. 193-198 (1994).

Levy, et al., "Effect of ultrasound on transdermal drug delivery to rats and guinea pigs", *J. Clin. Invest.*, 83:2074-2078 (1989).

Liu, et al., "Experimental Approach to Elucidate the Mechanism of Ultrasound-enhanced Polymer Erosion and Release of Incorporated Substances," *Macromolecules*, 25:123-128 (1992).

Liu, et al., "Cotransport of Estradiol and Ethanol Through Human Skin In Vitro: Understanding the Permeant/Enhancer Flux Relationship," *Pharm. Res.*, 8:938-944 (1991).

Machluf and Kost, "Ultrasonically Enhanced transdermal drug delivery, Experimental approaches to elucidate the mechanism," *J. Biomater. Sci. Polymer Edn*, 5:147-156 (1993).

Mak, et al., "Oleic Acid Concentration and Effect in Human Stratum Corneum: Non-Invasive Determination by Attenuated Total Reflectance Infrared Spectroscopy in Vivo", *J. Control. Rel.*, 12:67-75 (1990).

Mezei, "Liposomes as a Skin Drug Delivery System," Topics in Pharmaceutical Sciences, pp. 345-357 (1985).

Mitragotri, et al., "A Mechanistic Study of Ultrasonically-Enhanced Transdermal Drug Delivery," *J. Pharm. Sci.*, 84(6):697-706 (1995).

Mitragotri, et al., "Ultrasound-Mediated Transdermal Protein Delivery,"*Science*, 269:850-853 (1995).

Mitragotri, et al., "Sonophoresis: Enhanced Transdermal Drug Delivery by Application of Ultrasound," *Encyclopedia of Pharmaceutical Technology*, 14:103-122 (1996).

Mitragotri et al., "Synergistic Effect of Low-frequency Ultrasound and Sodium Lauryl Sulfate on Transdermal Transport," *J. Pharm. Sci.*, 89(7):892-900 (2000).

Mitragotri, "Synergistic Effect of Enhancers for Transdermal Drug Delivery," *Pharm Res.*, 17(11):1354-1359 (2000).

(56) References Cited

OTHER PUBLICATIONS

Mitragotri & Kost, "Transdermal Delivery of Heparin and Low-Molecular Weight heparin Using Low-frequency Ultrasound," *Pharm. Res.*, 18(8):1151-1156 (2001).

Miyakazi, et al., "Controlled Drug Release by Ultrasound Irradiation," *Chemical & Pharmaceutical Bulletin*, 33(1):428-431 (1985).

Monti, et al., "Comparison of the effect of ultrasound of Chemical enhancers on transdermal permeation of caffeine and morphine through hairless mouse skin in vitro," *International J. Pharmaceuticals*, 229( 1-2): 131-137 (Oct. 2001).

Morimoto, et al., "Prediction of Skin Permeability of Drugs: Comparison of Human and Hairless Rat Skin," *J. Pharm. Pharmacol.* 44: 634-639 (1991).

Murav'ev, et al., "Mechanism of the Release of Pharmaceutical Substances from Ointment bases by ultrasound," Chemical Abstacts, vol. 84, No. 4, p. 333, Abstract No. 22054g (Jan. 26, 1976).

Nagai, et al., "Buccal/Gingival Drug Delivery Systems," *J. Control. Rel.*, 6:353-360 (1987).

Newman, et al., "Hydrocortisone Phonophoresis," *J. Am. Pod. Med. Assoc.* 82:432-435 (1992).

Olanoff &Gibson, "Method to Enhance Intranasal Peptide Delivery," Controlled Release Technology Pharmaceutical Application (Lee, et al. Editors, American Chemical Society), pp. 301-309 (1987).

Ongpipattanankul, et al., "Evidence that Oleic Acid Exists in a Separate Phase Within Stratum Corneum Lipids," *Pharm. Res.*, 8:350-354 (1991).

Otsuka, et al., "Use of Ultrasonic Waves in Pharmacy—I & II. Degradation of Polymers," *Chemical Abstracts*, vol. 69, No. 20, pp. 7513, Abstract No. 80161r & No. 80162 (Nov. 11, 1968).

Pishko, et al., "Amperometric Glucose Microelectrodes Prepared through Immobilization of Glucose Oxidase in Redox Hydrogels", *Anal. Chem.*, 63:2268-2272 (1991).

Potts & Guy, "Predicting Skin Permeability", *Pharm. Res.*, 9:663-669 (1992).

Prausnitz, et al., "Electroporation of mammalian skin: A mechanism to enhance transdermal drug delivery", *Proc. Natl. Acad. Sci. USA*, 90:10504-10508 (1993).

Quillen, "Phonophoresis: A Review of the Literature and Technique", *Athl. Train.*, 15:109-110 (1980).

Remington's Pharmaceutical Sciences, Chapter 19—Disperse Systems pp. 267-272 Chapter 87—Medicated Appliances pp. 1600-1606, 1614 Chapter 91—Sustained-Release Drug Delivery Systems pp. 1690-1693, Mack Publishing Co, Easton PA (1990).

Robinson & Lee, "Influence of Drug Properties on Design", In:Controlled Drug Delivery, Mercer Dekker, Inc. N.Y. (1987), pp. 42-43.

Rosell, et al., "Skin Impedance From 1 Hz to 1 MHz", *IEEE Trans. Biomed. Eng.*, 35:649-651 (1988).

Schreier & Bouwstra, "Liposome and noisomes as topical drug carriers: dermal and transdermal drug delivery", *J. Control. Rel.*, 30:1-15 (1994).

Skauen, et al., "Phonophoresis", *Int. J. Pharm.* 20:235-245 (1984).

Tamada, et al., "Correlation of blood glucose with iontophoretic glucose flux in human subjects for glucose monitoring", *Proceed. Intern. Symp. Control. Rel. Bioact. Mater.* 22:129-130 (1995).

Tang, et al., "Theoretical description of transdermal transport of hydrophilic permeants: application to low-frequency sonophoresis" *J Pharm Sci.*, 90(5):545-68 (2001).

Tezel, et al., "Synergistic effect of low-frequency ultrasound and surfactants on skin permeability", *J Pharm Sci.*, 91(1):91-100 (2002).

Tierney, et al., "The GlucoWatch biographer: a frequent automatic and noninvasive glucose monitor", *Annals of Medicine*, 32(9):632-641 (2000).

Tocanne, et al., "Lipid lateral diffusion and membrane organization", *FEBBS Lett.*, 257:10-16 (1989).

Tyle & Agrawala, "Drug Delivery by Phonophoresis", *Pharm. Res.*, 6:355-361 (1989).

Veillard, et al., "Buccal Controlled Delivery of Peptides" *Proceed. Intern. Symp. Control. Rel. Bioact. Matter.*, 14:22 (1987).

Walker & Hadgraft, "Oleic acid—a membrane 'fluidiser' or fluid within the membrane", *Int. J. Pharm.*, 71:R1-R4 (1991).

Walmsley, "Applications of Ultrasound in Dentistry", *Ultrasound in Med. and Biol.*, 14:7-14 (1988).

Walters, "Penetration Enhancers and Their Use in Transdermal Therapeutic Systems", in: Transdermal Drug Delivery: Developmental Issues and Research Initiatives, pp. 197-246 (Hadgraft J., Guy, R.H., Editors, Marcel Dekker, 1989).

Wester & Maibach, "Animal Models for Percutaneous Absorption", Topical Drug Bioavailability Bioequivalence and Penetration (Shah and Maibach, Editors, Plenum Press, New York), pp. 333-349, (1993).

Wheatley, et al., "Use of Ussing Chamber for Investigation of Drug Delivery Across Viable Nasal Tissue Membranes", *Proceed. Intern. Symp. Control. Rel. Bioact. Mater.* 14:26-27 (1987).

Williams, et al., "On the non-Gaussian distribution of human skin permeabilities", *Int. J. Pharm.*, 86:69-77 (1992).

Wilschut, et al., "Estimating Skin Permeation, The Validation of Five Mathematical Skin Permeation Models", *Chemosphere*, 30:1275-1296 (1995).

Egorov, et al. "Use of the Variants of the Pharmacophysical Influence in Ophthalmology," *Vestn Oftalmol.*, 108(2):52-4 (1992).

Friedman, "Interferons:A Primer", ISBN 0-12-268280-7 (Academic Press, NY 1981).

Japanese Office Action JP 2009/552888 mailed May 17, 2013, English Translation.

\* cited by examiner

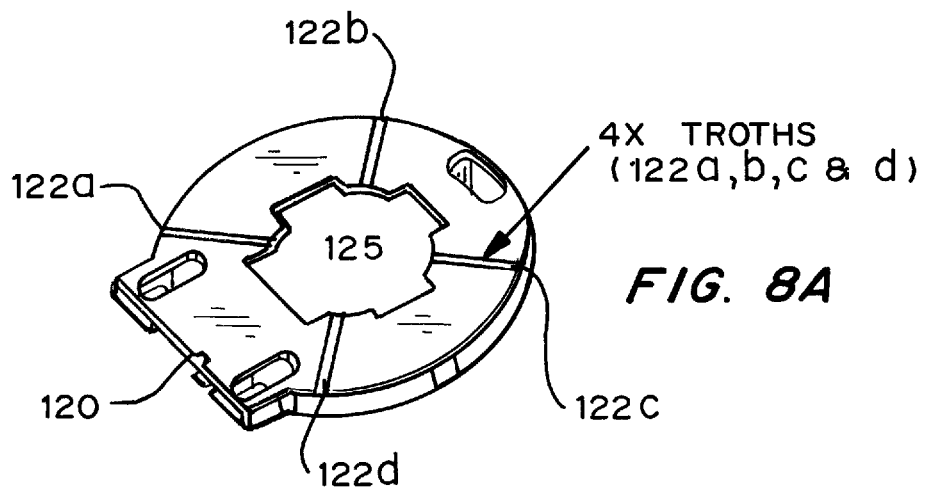
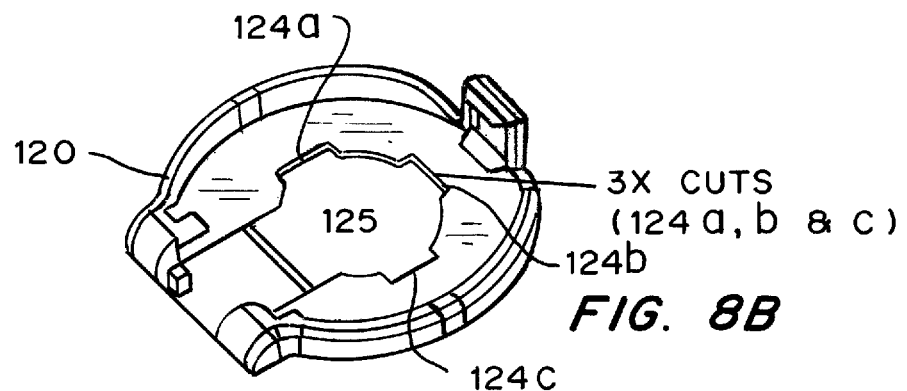
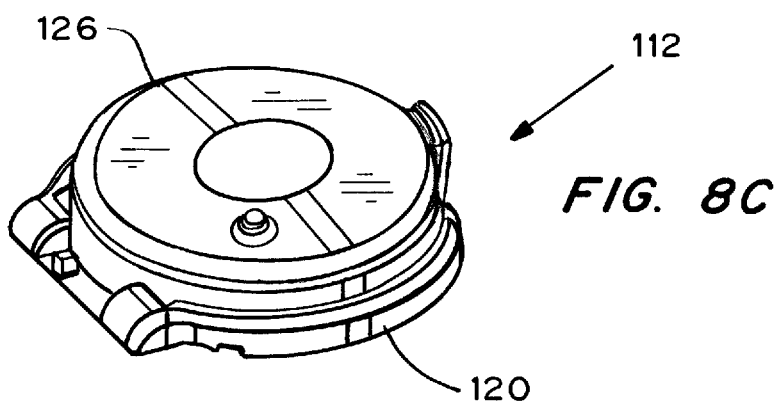

TRANSDERMAL ANALYTE MONITORING SYSTEMS AND METHODS FOR ANALYTE DETECTION

CROSS-REFERENCE TO RELATED APPLICATION

This application claims priority to U.S. Ser. No. 60/893,563, filed Mar. 7, 2007. The disclosures in the application listed above is herein incorporated by reference.

FIELD OF THE INVENTION

The present invention is directed to the field of systems and methods for improving non-invasive sampling of biological fluids, and more specifically to systems and methods for improving transdermal analyte detection and quantification.

BACKGROUND OF THE INVENTION

The impact that diabetes has on the health of Americans is staggering. According to the American Diabetes Association in 2006 approximately 20.8 million Americans were diagnosed with diabetes. The cost of diabetes in 2002 was estimated at $132 billion. The number of deaths in 2006 attributed to complications associated with diabetes was estimated at 613 Americans per day.

New and improved systems and methods for treating and detecting diabetes are in high demand. Analytical biosensors provide one type of system that can be used to manage diabetes. Analytical biosensors have been embraced during the last decade as a means of combining the advantages of electrochemical signal transduction with the specificity inherent in biological interactions. For example, the use of continuous glucose monitoring (CGM) to manage diabetes is becoming increasingly popular.

Despite recent improvements in analytical biosensor systems, the available systems suffer from disadvantages. For example, systems employing a hydrogel sensor typically have short shelf lives and may leak sensor materials onto the skin of a user. Alternatively, bacterial growth or growth of other microorganism can contaminate or foul the biosensor rendering its measurements of analytes unreliable. In some instances, proteins, carbohydrates, cells, or fragments of cells from the user can bind to the sensor and interfere with measurements. Such binding can also contaminate the biosensor.

Membranes, films or other physical barriers have been used on the surface of sensor electrodes to impede contaminants from reaching the face of the electrode. Typical films which have been employed include cellulose acetate, poly(o-phenylenediamine), polyphenol, polypyrrole, polycarbonate, and NAFION®, i.e. tetrafluoroethylene-perfluoro-3,6-dioxa-4-methyl-7-octenesulfonic acid copolymer (E.I. du Pont de Nemours & Co., Wilmington, Del.). However, these membranes can be difficult to prepare and may not efficiently attach to the reactive surface of the electrode.

Some CGM systems require pretreatment of the skin with a hydrating formulation prior to attachment of the system. For example, with existing biosensor systems, a 10-40 minute skin hydration procedure is typically applied to the target skin site after treatment to increase skin porosity and before sensor application. The hydration procedure results in better sensor performance than is achieved without pretreatment (sensor signal follows well to reference blood glucose reading). Although it enables improved sensor performance, the skin hydration procedure requires undesirable labor, materials and time which may further complicate the procedure for device installation, and hence the cost of the system. Systems that do not require complicated or time consuming skin pretreatment procedures are desirable.

In still other CGM systems, a standard reference glucose method is used to calibrate the glucose sensor and then the sensor reports subsequent glucose readings based on the calibrated electrical signal. In principle, the blood glucose concentration of a test subject should be proportional to the measured electrical signal. For sensors based on the enzymatic conversion of glucose, for example where the enzyme glucose oxidase (GOx) utilizes water and oxygen to convert glucose into hydrogen peroxide ($H_2O_2$) and glucolactone, the enzymatic conversion is limited by the amount of available oxygen. When the supply of oxygen is limited, such as in interstitial fluid, the concentration of glucose exceeds the concentration of oxygen, the enzymatic conversion of glucose will be dependent on the oxygen supply, resulting in unreliable sensor glucose reading and hence affecting the sensor performance.

Various methods have been reported to mitigate the issue of oxygen limitation. Tierney et al. describes using reverse iontophoresis to limit glucose extraction, maintaining desirable oxygen to glucose balance (M. Tierney et al., Annals of Medicine, 32(9):632-641 (2000)). U.S. Pat. No. 7,110,803 to Shults et al. discloses using a glucose-limiting membrane layer that has a high oxygen to glucose permeability ratio. U.S. Pat. No. 7,108,778 to Simpson et al. discloses using an auxiliary electrode to generate oxygen for the sensing chemistry. However, each of these methods requires the addition of extra elements to the CGM system, thereby increasing the cost and complexity of the system. A simple method for increasing the amount of available oxygen to the sensor without increasing the cost and complexity of the system is needed.

Therefore, it is an object of the invention to provide an improved transdermal analyte monitoring system.

It is another object to provide a method for reducing biofouling and/or contamination in a transdermal analyte monitoring system.

It is another object to provide methods for improving the accuracy of detection and/or quantification of an analyte by a transdermal analyte monitoring system.

SUMMARY OF THE INVENTION

Transdermal analyte monitoring systems (TAMS) with improved longevity and analyte detection are described herein. Generally, the transdermal analyte detecting system ("TADS") contains a sensor assembly, which includes (1) a hydrophilic polymer substrate, such as a hydrogel, designed to receive an analyte from the skin, and (2) a sensor body containing a plurality of electrodes, and a display and/or computing device. In the preferred embodiment, the TAMS includes a semi-permeable membrane at the end of the sensor, which attaches to the hydrophilic polymer substrate. This membrane interfaces with an exterior surface of a test subject and acts as a barrier between the patient's skin and the hydrophilic polymer substrate. The semi-permeable membrane reduces the amount of biological contamination of the hydrophilic polymer substrate, as compared to the same device in the absence of a semi-permeable membrane, by forming a protective barrier over the exposed surface of the hydrophilic polymer substrate. Additionally, the semi-permeable membrane prevents the hydrophilic polymer substrate from leaking out of the device. The hydrophilic polymer substrate typically includes an enzyme, and optionally includes one or more humectants.

In a preferred embodiment, the TAMS contains one or more channels or pockets in the sensor assembly, which increases the amount of oxygen available for reacting the analyte with an enzyme and generating a detectable signal.

In another embodiment, a method for improving analyte detection and/or quantification by a transdermal analyte monitoring system is provided. The method includes treating a region of skin of the organism to increase porosity and subsequently wiping the treated area of skin with a substrate. The substrate can be any suitable absorbent material, such as a pad, woven or non-woven fabric, felt, or gauze. Generally, the substrate contains a wiping reagent, such as a solvent (e.g. water, ethanol, or isopropanol), phosphate buffered saline, lactic acid, soap, a surfactant, or a combination thereof. The wiping step prevents the need for a skin hydration step. After the skin is wiped, the transdermal analyte monitoring system is applied.

In another embodiment, a kit containing a transdermal analyte detection system and a substrate is provided. The substrate may be impregnated with a wiping reagent. Alternatively, wiping reagents can be separately included in the kit.

BRIEF DESCRIPTION OF THE DRAWINGS

FIG. 8A shows a diagram of the bottom of an exemplary target plate with four air channels.

FIG. 8B shows a diagram of a front view of an exemplary glucose sensor's target plate with three cuts of internal air pockets surrounding the central hole for hydrogel chemistry.

FIG. 8C shows a diagram of an exemplary sensor housing on top of the target plate to provide an enclosed glucose sensor.

DETAILED DESCRIPTION OF THE INVENTION

I. Transdermal Analyte Monitoring System

Systems and methods for enhancing transdermal analyte detection are described herein. Generally, the transdermal analyte monitoring system ("TAMS") contains a sensor assembly, which includes (1) a hydrophilic polymer substrate, such as a hydrogel, designed to receive an analyte from the skin, and (2) a sensor body containing a plurality of electrodes, and a display and/or computing device. In the preferred embodiment, the TAMS includes a semi-permeable membrane at the end of the sensor, which attaches to the hydrophilic polymer substrate. This membrane acts as a semi-permeable barrier between the patient's skin and the hydrophilic polymer substrate.

The TAMS is applied to an area on the skin of an animal; typically the animal is a mammal, and in the preferred embodiment the mammal is a human.

When the system is used, the hydrogel contains enzymes that react continuously with the analyte, thereby generating an electrical signal. Then the electrical signal is detected by the electrode assembly. The electrical signal correlates with an analyte value.

The analyte to be monitored can be any analyte of interest, including, but not limited to glucose, lactate, blood gases (e.g. carbon dioxide or oxygen), blood pH, electrolytes, ammonia, proteins or any other biological species that is present in a biological fluid, such as blood, plasma, serum or interstitial fluid.

Figure 1:
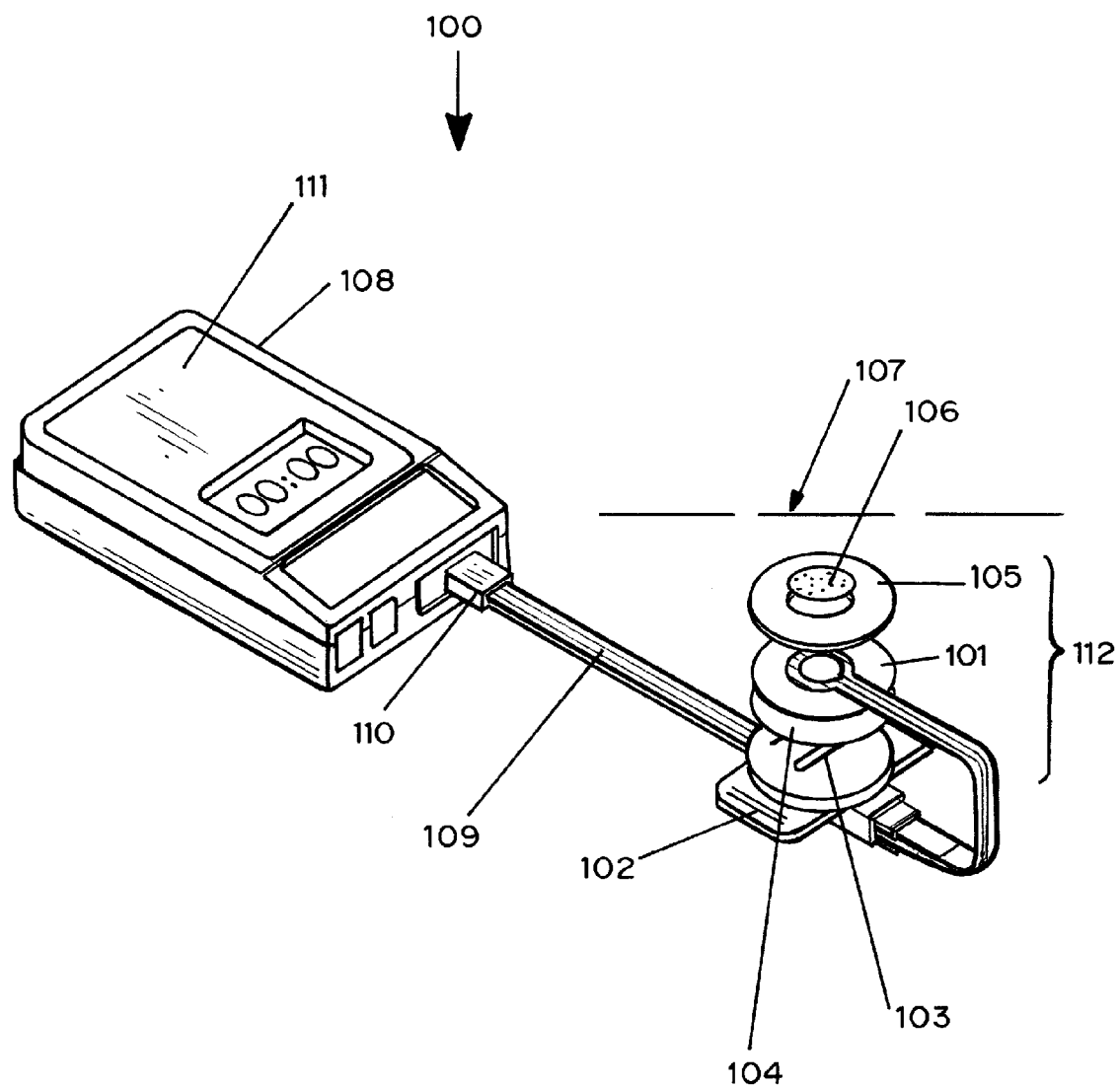
FIG. 1 shows an exemplary wired transdermal analyte monitoring system (TAMS) for performing continuous analyte monitoring, with the sensor illustrated in an exploded view. Alternatively, the communication between the sensor and the monitor can be achieved through a wireless link (not shown in FIG. 1).

An exemplary TAMS is described in U.S. Publication No. 20060094946 to Kellogg et al. and is illustrated herein in FIG. 1. The TAMS shown in FIG. 1 can be used to carry out continuous monitoring of an analyte, such as glucose. As shown in FIG. 1, the TAMS (100) contains a sensor assembly (112), which includes a sensor body (101), a hydrogel disc (106) and a mounting plate (102) as well as other components as described herein, which may be attached to a display or computing device. During operation, the sensor assembly (112) may be positioned adjacent a permeable region (107) of a user's skin as shown by the dashed line in FIG. 1. The sensor assembly (112) may be attached by any suitable means to a display or computing device. Suitable means include a wireless connection or any other means for electrical connection, such as a flexible connecting cable (109). In an embodiment, the sensor assembly (112) is attached to a potentiostat recorder (108), which may include a printed circuit board (111). The connecting cable (109) preferably attaches to the potentiostat recorder (108) using a connector (110) that facilitates removal and attachment of the sensor assembly (112). Suitable means for attachment include a flexible connecting cable (109) and a wireless connection.

Figure 9:
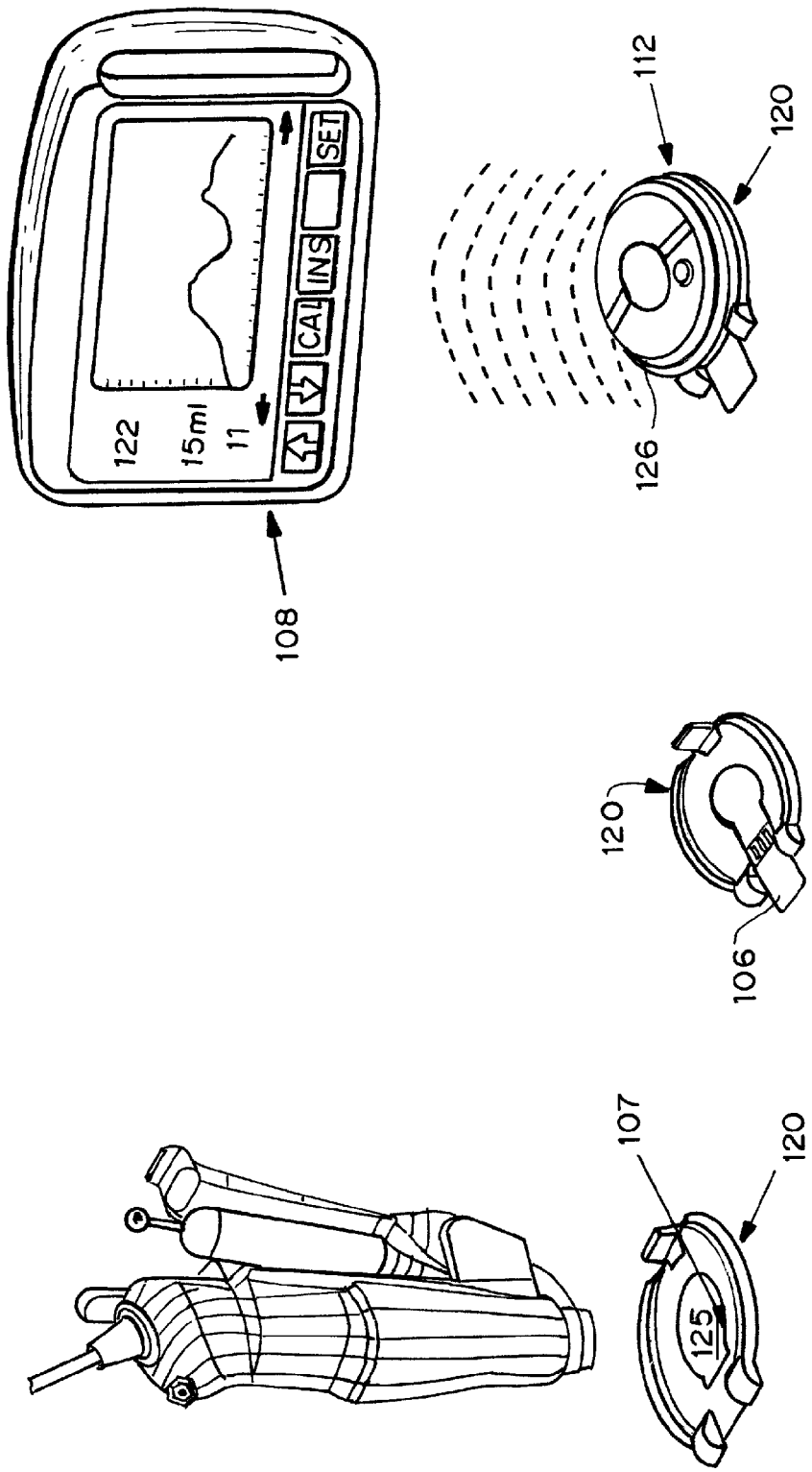
FIG. 9 is a schematic showing how to use an exemplary wireless transdermal analyte monitoring system (TAMS) for performing continuous analyte monitoring. This system could be used with the glucose sensor illustrated in FIGS. 8A, 8B, and 8C.

A TAMS with a wireless connection is illustrated in FIG. 9. The sensor assembly (112) includes a target plate (120), a hydrogel (106) and sensor, and a sensor housing (126). The sensor is coupled with a miniature analyzer which sends data wirelessly to a monitor for data processing and display.

A. Sensor Assembly

Figure 2:
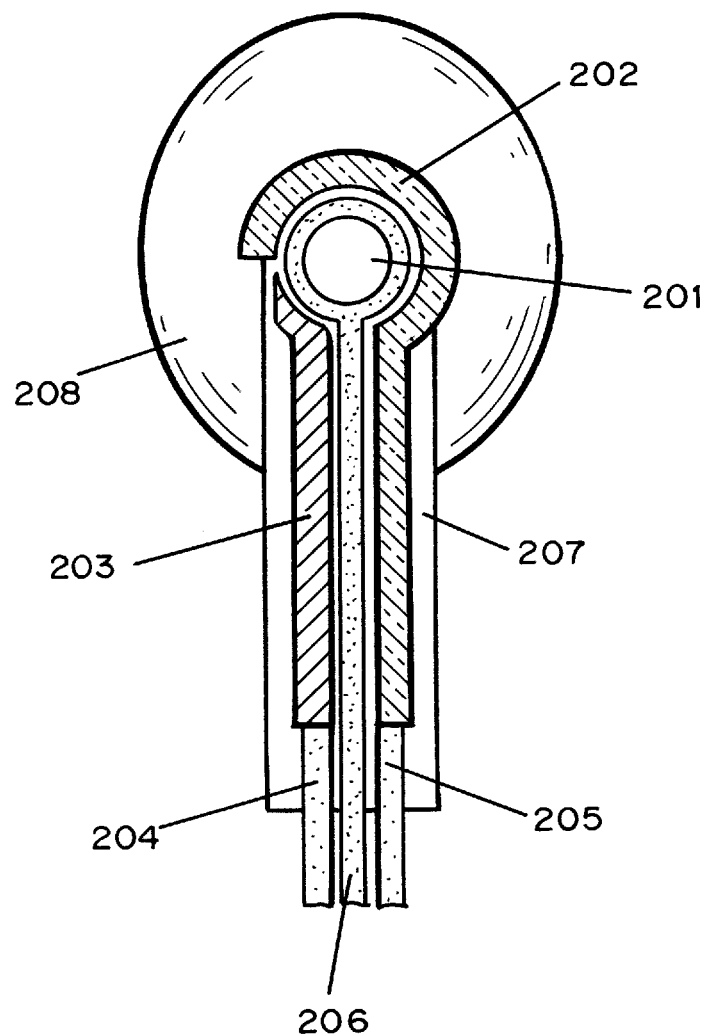
FIG. 2 shows a drawing of the sensor body shown in FIG. 1.

The sensor assembly (112) shown in FIGS. 1 and 2 may be incorporated into any one of a number of detection devices. For instance, this sensor assembly may be incorporated into the receiver to provide for discrete and/or continuous glucose monitoring.

The sensor assembly (112) includes a sensor body (101). The sensor body may include electrodes, as shown in FIG. 2, on its surface for electrochemical detection of analytes or reaction products that are indicative of analytes.

A thermal transducer (103), which may be housed within the sensor assembly (112) with a shape that corresponds to that of the sensor body (101), is located between the sensor body (101) and the mounting plate (102). Enzyme-based electrochemical sensors, such as glucose sensors, can be sensitive to temperature fluctuation. The thermal transducer (103) may be used to normalize and report only those changes attributed to a change in analyte or analyte indicator.

The sensor assembly (112) may also contain an adhesive disc (104), which may be attached to the side of the sensor body (101) that faces the thermal transducer (103).

The sensor assembly (112) may also contain an adhesive ring (105), which may be attached to the side of the sensor body (101) that is opposite the adhesive disc (104). The cut-out center portion of the adhesive ring (105) preferably exposes some or all of the sensor components on the sensor body (101). The adhesive ring (105) and adhesive disc (104) may have a shape that corresponds to that of the sensor body as shown in FIG. 1.

The sensor assembly (112) contains a hydrogel disc (106), which may be positioned within the cut-out center portion of the adhesive ring (105) adjacent to a surface of the sensor body (101).

a. Sensor Body

A sensor body (101) is illustrated in detail in FIG. 2. The sensor body 101 includes a body layer (207) upon which leads (204, 205, and 206) are patterned. The leads may be formed, for example, by coating metal over the body layer (207) in the desired locations. A working electrode (201), is typically located at the center of the sensor body (101). The working electrode (201) may contain a catalytic and/or conductive material, such as pure platinum, platinized carbon, glassy carbon, carbon nanotube, mezoporous platinum, platinum black, paladium, gold, or platinum-iridium. The working electrode (201) may be patterned over lead (206) so that it is in electrical contact with the lead (206). A counter electrode (202) may contain a stable and conductive material, and preferably contains carbon, which may be positioned about the periphery of a portion of the working electrode (201), as shown in FIG. 2. The counter electrode (202) may be patterned over lead (205) so that it is in electrical contact with the lead (205). A reference electrode (203) containing binary oxi-reductive materials which provide consistent redox potential, preferably containing Ag/AgCl, may be positioned about the periphery of another portion of the working electrode (201), as shown in FIG. 2. The electrodes (201, 202, and 203) can be formed to roughly track the layout of the electrical leads (206, 205, 204), respectively, that are patterned in the sensing area of the device. The electrodes (201, 202, and 203) may be screen printed or sputter coated over the electrical leads (206, 205, 204), respectively. The leads can be patterned, using screen printing or other methods known in the art, onto the sensor body (101) in a manner that permits electrical connection to external devices or components. For example, the leads may form a 3× connector pin lead including leads (204, 205, and 206) at the terminus of an extended region of the sensor body, as shown in FIG. 2. A standard connector may then be used to connect the sensor electrodes to external devices or components.

b. Hydrophilic Polymer Substrate

The sensor assembly contains a hydrophilic polymer substrate. The substrate is designed to provide the structure to form an aqueous reservoir in the sensor assembly. The hydrophilic polymer substrate may be in any suitable shape that fits in the sensor assembly. Typically, the hydrophilic polymer substrate is in the shape of the sensor body. A standard form is a disc. The shape is selected to co-ordinate with the shape of the sensor. Optionally, ionic moieties can be incorporated into the hydrophilic polymer substrates to impart added functionalities, such as bioadhesiveness. In the preferred embodiment, the substrate is a hydrogel.

Hydrogels are a class of biomaterials utilized for medical and biotechnological applications, such as in contact lenses, biosensors, linings for artificial implants and drug delivery devices. The transdermal analyte monitoring system may utilize one or more of the hydrogel materials described below. Classes of hydrogel materials that may be used in the sensor assembly include agarose based hydrogels, polyethylene glycol diacrylate (PEG-DA)-based hydrogels, and vinyl acetate-based hydrogels including polyethylene glycol diacrylate/ polyethyleneimine (PEGDA-PEI) and polyethylene glycol diacrylate-n-vinyl pyrrolidone (PEGDA-NVP).

Suitable polymers which can form a hydrogel include, but are not limited to, synthetic or natural polymers. Examples of synthetic polymers include polyacrylic and polymethacrylic acid polymers, cellulose derivatives such as hydroxypropyl cellulose, polyethyleneglycol polymers, copolymers and block copolymers, and other water swellable, biocompatible polymers. Examples of natural polymers include collagen, hyaluronic acid, gelatin, albumin, polysaccharide, and derivatives thereof. Natural polymers can also be of the type isolated from various plant materials such as psyllium.

Structurally, the polymeric hydrogels are three-dimensional macromolecular configurations. They may be produced through several methods: a) synthesis from monomers (cross-linking polymerization); b) synthesis from polymers and polymerization auxiliary (grafting and cross-linking polymerization); c) synthesis from polymers and non-polymerization auxiliary (cross-linking polymers); d) synthesis from polymers with energy sources (cross-linking polymers without auxiliaries) and e) synthesis from polymers (cross-linking by reactive polymer-polymer intercoupling).

The hydrogels can vary in thickness. Typically the hydrogel is about 10 to about 1000 μm, more preferably about 50 to about 700 μm, even more preferably about 200 to about 500 μm.

As shown in FIG. 1, a hydrogel disc (106) may be positioned in such a manner that it will face toward the user after folding over onto the mounting plate (102). The sensor body (101) may be connected to the mounting plate (102) using standard connectors with a latch that mates with a corresponding connector interface that is mounted onto the backing plate (102).

i. Agarose-Based Hydrogels

Agarose based hydrogels can offer advantages for continuous transdermal analyte monitoring. For instance, agarose-based hydrogels offer one or more of the following features: good response to glucose and hydrogen peroxide due to its high water content, high enzyme loading, good biocompatibility, and excellent permeation and diffusion properties. Agarose based hydrogels are generally compatible with water-soluble analytes. In addition, agarose hydrogels are clean, inexpensive, and/or easy to prepare.

An agarose gel may be formed, for example, from 1-20% agarose in buffer solution containing 0-1 M sodium or potassium phosphate, 0-1 M sodium chloride, 0-1 M potassium chloride, 0-2 M lactic acid, surfactant such as 0-1 M TRITON® X-100 (Union Carbide Chemicals & Plastics Technology Corp.), TWEEN® 80 (ICI Americas Inc.) or sodium lauryl sulfate, and any other biocompatible components. Loading of glucose oxidase in agarose hydrogel can be up to 0-20% (by weight), for example, by soaking the solid hydrogel in concentrated glucose oxidase solution, or alternatively by mixing concentrated glucose oxidase powder or solution with agarose solution during its melting stage (15-65° C.), followed by cooling and gelling at lower temperature (40° C. or lower).

ii. PEG-Based Hydrogels

PEG-based hydrogels can offer several advantages for continuous transdermal analyte monitoring. Structurally, PEG is highly hydrophilic and presents a high degree of solvation in aqueous solvents. The preferential solvation of PEG molecules can effectively exclude proteins from the PEG chain volume, thereby protecting the surface from bio-fouling by proteins. An advantage that can be provided by chemically crosslinked PEG-based hydrogels is that their physical and chemical properties can be modulated by varying the molecular weight of the PEG chains and varying the initiator concentration. For example, increasing the molecular weight of the polyethylene oxide backbone increases the network mesh size. The release of a bioactive molecule, such as an enzyme, can be controlled by control of the network density. Therefore, a hydrogel containing PEGs of a weight average molecular weight of 8 KDa would have a higher rate of release of an entrapped drug than a hydrogel containing PEGs of a weight average molecular weight of 3.3 KDa.

Optionally, additives can be incorporated into the hydrogels to impart added functionalities, such as bioadhesiveness. For example, hyaluronic acid or polyacrylic acid can be added to the PEG macromer prior to crosslinking to create bioadhesive hydrogels. In another example, an ionic character can be imparted to the crosslinked hydrogels to provide molecular interaction (e.g. ionic bonds) with entrapped drugs to slow down rates of release of drug from the matrix.

PEG-based hydrogels used in biosensors can provide one or more of the following features: (a) a biocompatible, non-biofouling surface appropriate for long-term exposure to biological fluids without compromise of sensor function, (b) a reservoir for glucose oxidase, (c) a matrix that can be incorporated with ionic moieties to enhance entrapment of glucose oxidase, (d) a matrix that can be modulated in terms of its physical and chemical properties (network density, swelling) by varying the molecular weight of the backbone and (e) a matrix that can be rendered bioadhesive by addition of ionic excipients such as chitosan gluconate, polyacrylic acid, poly (amidoamine), poly(ethyleneimine) and hyaluronic acid.

When the hydrogel is formed from a polyethyleneglycol diacrylate (PEGDA) macromer, polymerization, such as UV polymerization, may occur in a mold that contains a preloaded scrim page, which provides a support matrix and a handle for the hydrogel. The PEGDA macromer polymerizes only around the circular head portion of the lollipop-shaped page, leaving the tail section of the page hydrogel-free and useful as a handle (see FIG. 2 and FIG. 9).

Optionally, the PEDGA hydrogel includes an acrylate-PEG-NHS (A-PEG-N) reagent (e.g. sold by Nektar), which can function as a linker molecule to covalently link an enzyme, such as the GOx enzyme, to the PEGDA hydrogel network.

iii. Vinyl Acetate-Based Hydrogels

Vinyl acetate-based hydrogels, such as n-vinylpyrrolidone/vinyl acetate copolymer, can exhibit features such as transparency, tackiness, non-toxicity, flexibility, and/or hydrophobicity. Vinyl acetate-based hydrogels typically have a good ability to retain moisture and entrap enzymes, such as glucose oxidase, are biocompatible, and adhere-well to skin to improve skin-sensor coupling. As reported by Chuang et al., glucose flux sensor using n-vinylpyrolidone/vinyl acetate copolymer as the hydrogel showed good performance in tracking the plasma glucose levels of a patient with diabetes during a glucose clamping study. Chuang, et al., "*Ultrasonic Pretreatment Enables Continuous Transdermal Glucose Monitoring*", Presented at the 4th Annual Diabetes Technology Meeting Held Oct. 28-30, 2004, (Philadelphia, Pa.).

iv. Modified Hydrogels

1. Covalently Immobilized Enzymes

Optionally, the hydrogels may be modified to include enzymes and/or humectants. The enzymes and/or humectants may be entrapped by any suitable means, including covalent bonding and non-covalent immobilization. Examples of non-covalent immobilization include, but are not limited to ionic interactions and physical entrapment. Preferably the enzymes are covalently linked to the hydrogel, such as by using a linker molecule. In one embodiment, particularly suitable for use in a CGM system, glucose oxidase is covalently immobilized in the hydrogel disc. For example, covalent immobilization of GOx into a PEGDA network improves the effective performance of the device by eliminating GOx diffusion (maintaining bioavailability) and/or by stabilizing the enzyme (maintaining bioactivity). The PEGDA network provides the structure to contain ~80% water within its matrix. It acts as an aqueous reservoir to hold vital components in solution (e.g., buffer salts and osmotic agents), and also provides a transport medium for the diffusion of the analyte.

At a 15% (w/w) PEGDA concentration, most of the GOx can be retained in the hydrogel by physical entrapment in the mesh. However, at lower PEGDA concentrations, such as those approaching 10% (w/w), the more open mesh will not retain GOx, and covalent immobilization is necessary.

Covalently Linking the Enzyme to the Hydrogel Using a Linker

The coupling of the enzyme to the hydrogel may also be accomplished using a linker. The linker molecule generally contains two or more functional groups which are able to react with functional groups on the enzyme and functional groups on the hydrogel. For example, the linker molecule may contain electrophilic groups which react with nucleophilic groups found in the enzyme and hydrogel, such as hydroxy, thiol, and/or amino groups. These linkers mediate the conjugation of the enzyme to the surface of the hydrogel by forming a bond containing a variable number of atoms. The linker molecules can be homofunctional (i.e., the functional groups are identical) or heterofunctional (i.e., the functional groups are different).

Suitable linker molecules include, but are not limited to, N-Succinimidyl 3-(2-pyridyldithio)propionate (SPDP, 3- and 7-atom spacer), long-chain-SPDP (12-atom spacer), (Succinimidyloxycarbonyl-α-methyl-2-(2-pyridyldithio)toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(γ-maleimidobutyryloxy)succinimide ester (GMBS, 8-atom spacer), N-(γ-maleimidobutyryloxy)sulfosuccinimide ester (sulfo-GMBS, 8-atom spacer), Succinimidyl 6-((iodoacetyl)amino)hexanoate (SIAX, 9-atom spacer), Succinimidyl 6-(6-(((4-iodoacetyl)amino)hexanoyl)amino) hexanoate (SIAXX, 16-atom spacer), 1,4-Di-[3'-2'-pyridyldithio)propion-amido]butane (DPDPB, 16-atom spacer), Bismaleimidohexane (BMH, 14-atom spacer), and p-nitrophenyl iodoacetate (NPIA, 2-atom spacer). One ordinarily skilled in the art also will recognize that a number of other coupling agents, with different number of atoms, may be used.

Moreover, spacer molecules may be incorporated into the linker to increase the distance between the reactive functional groups at the termini, such as acrylate-polyethylene glycol-N-hydroxy succinimide (acrylate-PEG-NHS or A-PEG-N). A number of multifunctional PEGs are commercially available from Shearwater Polymers (Huntsville, Ala.) and Texaco Chemical Co. (Houston, Tex.). Multi-amino PEGs are available under the name "Jeffamine" and include diamino PEGs and triamino PEGs. In the preferred embodiment, the enzyme is covalently immobilized in the hydrogel using an acrylate-PEG-NHS (A-PEG-N).

Covalently Linking the Enzyme to the Hydrogel Using a Coupling Agent

The enzyme can also be coupled directly to the hydrogel by the use of a reagent or reaction that activates a group on the surface of the hydrogel or the enzyme making it reactive with a functional group on the enzyme or hydrogel, respectively, without the incorporation of a coupling agent.

For example, carbodiimides mediate the formation of amide linkages between a carboxylate and an amine or phosphoramidate linkages between phosphate and an amine. Examples of carbodiimides are 1-ethyl-3-(3-dimethylaminopropyl)carbodiimide hydrochloride (EDC), 1-cyclohexyl-3-(2-morpholinoethyl)carbodiimide (CMC), dicyclohexyl carbodiimide (DCC), diisopropyl carbodiimide (DIC), and N,N'-carbonyldiimidazole (CDI). N-ethyl-3-phenylisoxazolium-3'-sulfonate (Woodward's reagent) mediates the formation of amide linkages though the condensation of carboxylates and amines. CDI can also be used to couple amino groups to hydroxyl groups.

2. Humectants

In another embodiment, the hydrogel is modified to contain one or more humectants. A humectant is a hygroscopic substance with a strong the affinity to form hydrogen bonds with molecules of water. The humectant typically has several hydrophilic groups, such as hydroxyl groups, amines or carboxyl groups. The hydrogel may contain any suitable amount of the humectant to ensure that the hydrogel retains the necessary level of water. Suitable amounts of the humectant in the hydrogel range from 0.1 to 40% (wt/wt), preferably the amount ranges from 5 to 15% (wt/wt).

Preferably the humectant contains an overall negative charge. Suitable anionic humectants include, but are not limited to, glyceryl triacetate, and negatively charged polyols. Preferred humectants that have been tested include sodium PCA (i.e., a sodium salt of 2-pyrrolidone-5-carboxylic acid) and sodium lactate.

Some small molecule humectants, i.e. molecules with molecular weights of less than 1000 Da, may be useful. Examples of useful small-molecule humectants include, but are not limited to, urea, propylene glycol, sodium lactate and sodium pyrrolidone carboxylic acid (PCA).

Some polysaccharide humectants are useful. Examples of useful polysaccharide humectants include, but are not limited to, hyaluronic acid (sodium salt), carrageenan and agarose.

Humectants retain water molecules that would otherwise evaporate from the open system over the period of application. A loss of water in the gel would cause any number of deleterious effects, among them, increased transport resistance, decreased bioavailability of the catalyst that provides the electrical signal (e.g. GOx enzyme), loss of interfacial contact area from shrinkage. Any one of the above effects can interfere with device performance.

Figure 5:
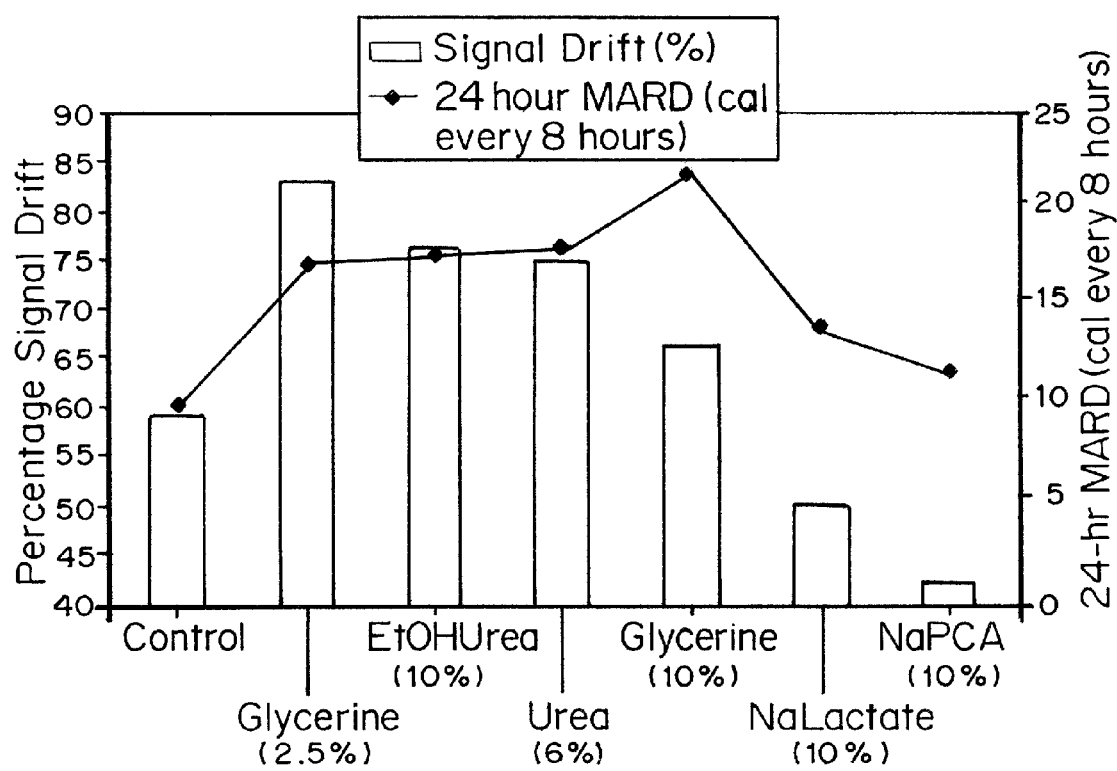
FIG. 5 shows a bar graph of signal drift (%) and 24-hr MARD when various humectants were included in the hydrogel matrix. Testing was 24-hr ex vivo application, and all used a 0.2PES.Naf membrane.

The humectant improves device consistency by mitigating water loss. Decreased water loss also improves the longevity of the device. As disclosed in Example 2, certain humectants have been shown to prolong device performance (as indicated by decreased signal drift) as compared to a control (without a humectant), while others, such as glycerol and hydroxyethyl urea, were did not increase device performance (as indicated by increased signal drift) as compared to a control (without a humectant) and hence were not beneficial. The preferred humectants increase the performance longevity of a device, while not significantly increasing the error in the readings (such as analyzed by MARD) (see FIG. 5).

c. Mounting Plate or Target Plate

The mounting plate (102) may have any suitable geometry. The mounting plate connects to the sensor body (101) using standard connectors such as a SLIM/RCPT connector with a latch that mates with a corresponding connector interface that is mounted onto the mounting plate (102). In the wireless system, such as shown in FIGS. 8A, 8B, and 8C, a target plate (120) is used in place of a mounting plate. Preferably, the mounting plate or target plate is formed from rigid, non-conductive materials with high dielectric constants, such as plastics, which provides firm backing for the sensor body (101) and secure housing for the hydrogel. Suitable materials for the mounting plate include the materials typically used for printed circuit boards, which not only provide firm backing for the sensor body (101) but also provide printed electrical circuit for the sensor system.

i. Air Pockets or Channels

In one embodiment, the sensor assembly used in the TAMS contains channels or pockets to enable air and/or oxygen to be supplied to the hydrogel or other elements in the sensor assembly that require oxygen to function. One or more air channels and pockets can be located around a hydrogel. The air channels (122) and/or pockets (124) are generally in the form of slits or openings on the mounting plate (102) of a wired system (FIG. 1) or the target plate (120) of a wireless system (see FIGS. 8A and 8B). The channels and pockets not only increase the supply of oxygen (enhanced oxygenation) but also maintain the hydrogel moisture (water). The air channels and pockets can be created by molding, milling, punching, etching or any other mechanical or chemical means.

FIGS. 8A-C show examples of air channels and pockets in the target plate (120) in a wireless TAMS. The wired system (shown in FIGS. 1 and 2) could be modified in a similar manner to include air pockets and channels. FIG. 8A shows a diagram of a rear view of an exemplary glucose sensor's target plate with four air channels (122A, B, C, and D). FIG. 8B shows a diagram of a front view of an exemplary glucose sensor's target plate with three cuts (124 A, B, and C) of internal air pockets surrounding the central hole (125) for hydrogel chemistry. FIG. 8C shows a diagram of an exemplary wireless sensor housing (126) on top of the target plate (120) to provide an enclosed glucose sensor assembly (112).

In one preferred embodiment, the TAMS includes sensors for transdermal analyte detection in which glucose oxidase (GOx, an enzyme) utilizes water and oxygen to convert glucose into hydrogen peroxide ($H_2O_2$) and glucolactone. An electrochemical glucose sensor can be designed by using a platinum electrode to break down $H_2O_2$ and in the mean time generating a continuous electrical current with continuous supply of transdermal glucose flux. If channels or pockets for air or oxygen are included in the sensor assembly, the amount of oxygen supplied to the hydrogel is increased compared to the same hydrogel in the absence of such air pockets or channels and the hydrogel's moisture level is maintained. This is essential for GOx to convert glucose to hydrogen peroxide, which is subsequently electrochemically oxidized and measured to determine the amount of glucose in the blood.

B. Semi-Permeable Membrane

In one preferred embodiment, the TAMS includes a protective, semi-permeable membrane between the surface of the hydrogel and the skin of the user. The protective, semi-permeable membranes can have different pore sizes, composition, charge, reactivity, and thickness. The pores can range from the macroporous (5 µm) to ultrafiltration (3 k) to undefined (NAFION®). "Undefined", as used herein, refers to membranes for which there is currently no standard manner to characterize their pore structure, such as NAFION®. NAFION® contains ionic channels, with sizes ranging from about 1 nm to about 50 nm, depending on the state of hydration For transdermal analyte monitoring systems, such as CGMs, the attachment of a protective semi-permeable membrane to the outer face of the hydrogel improves the device performance by extending its longevity and reducing contamination of the hydrogel with microorganisms, proteins, cellular material, etc. As an interface between the hydrogel and the porated skin, the membrane can reduce biological contaminants such as proteins, lipids, cellular debris, microorganisms, or combinations thereof.

The protective, semi-permeable membrane can be formed from a variety of polymers, copolymers, or blends thereof. Suitable polymers include hydrophobic polymers such as polytetrafluoroethylene (PTFE); hydrophilic polymers such as Nylon, polyethersulfones (PES), activated PES, (3-mercaptopropyl)trimethylsilane, cellulose acetate, electropolymerized films such as 1,8-diaminonapthaline and phenylenediamine, and NAFION®-coated PES. NAFION® (tetrafluoroethylene-perfluoro-3,6-dioxa-4-methyl-7-octenesulfonic acid copolymer) is a biocompatible anionic fluoropolymer that can be coated on the hydrogel as a protective layer against physiological contaminants and biofouling. NAFION® acts as a protective layer based on its hydrophobicity, charge selection, and/or size exclusion.

A semi-permeable membrane, such as in the form of a polymeric film, may be coated on an outer surface of the hydrogel layer (106). In general, one or more protective barrier layers may be provided between the hydrogel and the user's skin during operation. The polymer film can be coated on a hydrogel surface using any suitable method, such as by micropipette or by dip-coating the sensor in aqueous or organic polymer solution followed by air drying for several hours before use.

In another embodiment, the protective, semi-permeable membrane is attached to only one side of the hydrogel. The interfacial attachment is formed by polymerizing the hydrogel in the presence of the membrane, and forming an Interpenetrating Polymer Network (IPN) in the interfacial region. An IPN is formed when a first polymer (such as a PEGDA hydrogel) is cross-linked in the presence of another polymer network (such as, a polymeric membrane).

In one embodiment, the semi-permeable membrane is negatively-charged (e.g., NAFION®-coated PES) at the hydrogel/skin interface to prevent the loss of negatively-charged components from the hydrogel into the skin. Negatively-charged humectants (e.g., NaPCA) and osmotic agents (e.g., lactic acid) are often included in the hydrogel, and increase the stability of the system.

It is known that protective membranes bind proteins or other biological agents through covalent, electrostatic, hydrophobic, and/or mechanical interactions. As shown by in-house experiments (unpublished) when a membrane was applied between the skin and the hydrogel (during 12-hr ex vivo applications), a reduction of protein deposition on the hydrogel was observed. Using extractions and bicinchoninic acid (BCA) protein analysis, an average protein deposition of 32 µg per gel disc was observed without a membrane in place, and an average protein deposition of 14 µg per gel disc was observed when a protective membrane was used.

IV. Methods for Improving Analyte Detection

A. Skin Preparation

In one preferred method of using the TAMS, a skin preparation wipe is applied to the skin prior to application of the TAMS. This skin preparation wipe is used in place of the standard skin hydration procedure currently used in prior art methods. This skin preparation wipe is applied to wipe or clean the surface. It is typically applied to the target skin area by massaging, wiping, padding, rubbing or any other methods to clean the target skin site after a skin pretreatment to increase porosity. This step typically takes a short period of time (as compared to the longer standard hydration procedures used in the prior art), such as from about 1 to 30 seconds.

The wipe can be formed of a paper, cotton or textile based substrate soaked in agents containing water, phosphate buffered saline, lactic acid, soap, surfactant or any other chemicals, solvents or their mixtures which can be used to clean the target skin area after any skin pretreatment procedure, such as SonoPrep® Ultrasonic Skin Permeation System (Sontra Medical). Preferably, the agents are inorganic or organic solvents such as water, ethanol, isopropanol or a combination thereof. An exemplary formulation of the agent contains 30-95% of isopropanol in water and the wipe material is gauze.

a. Kits

In one embodiment, a kit contains a transdermal analyte detection system and a skin preparation wipe, optionally including wiping reagents such as phosphate buffered saline, lactic acid, soap, surfactant, or a solvent. In one embodiment, the substrate is presoaked with a wiping reagent. In another embodiment, the wiping reagent is provided as a separate component of the kit.

B. Improved Oxygenation of Biosensors

In one preferred embodiment, the sensor assembly is designed to increase oxygen supply to the hydrogel and/or other elements in the sensor assembly that require oxygen to function. Air channels and pockets can be located around a hydrogel. The air channels and pockets are generally in the form of slits or openings on the mounting plate (102) or target plate (FIG. 8). The channels and pockets not only increase the supply of oxygen (enhanced oxygenation) but also maintain the hydrogel moisture (water). Preferably, the mounting plate or target plate is formed from rigid, non-conductive materials with high dielectric constant, such as plastics, which provides firm backing for the sensor body and secure housing for the hydrogel. The air channels and pockets can be created by molding, milling, punching, etching or any other mechanical or chemical means.

IV. Methods of Use

The TAMS described herein can be used to monitor biological analytes, for example glucose blood concentrations of a user and/or to deliver therapeutic compounds, as needed. The TAMS is applied to an area on the skin of an animal; typically the animal is a mammal, and in the preferred embodiment the mammal is a human.

For example, a prediabetic or diabetic person can use the device to monitor their glucose blood concentration levels and deliver insulin as needed depending on those concentration levels. The insulin can be delivered by the user or by the device. Other analytes can also be monitored.

Continuous glucose monitoring can measure the blood concentration of glucose without relying on accumulation of body fluids in the sensor device. In continuous glucose monitoring, for instance, one may prefer to minimize accumulation of both glucose and hydrogen peroxide in the hydrogel so that the current measured by the electrochemical sensor is reflective of the glucose flux through the permeable region of skin in real-time. This advantageously permits continuous real-time transdermal glucose monitoring.

To use the transdermal analyte monitoring systems described herein, first, a region of skin on the user is made more permeable using any suitable method. Typical methods for increasing the skin's permeability include tape stripping, rubbing, sanding, abrasion, laser ablation, radio frequency (RF) ablation, chemicals, sonophoresis, iontophoresis, electroporation, application of permeation enhancing agents. For example, the skin pretreatment procedure can be the application of low energy ultrasound (e.g. SonoPrep® Ultrasonic Skin Permeation System) or controlled skin abrasion.

When a wireless TAMS is used, typically, the target plate (120) is placed on the skin at the site for increased permeability. Then the sin pretreatment procedure is applied. This method is particularly suitable for use with SonoPrep® as the skin permeation system.

In the preferred embodiment, after the skin pretreatment step, the treated skin is cleaned, such as by wiping or rubbing the treated area of the skin with a skin preparation wipe for a short period of time, such as from about 1 to 30 seconds.

Then the sensor assembly, such as that shown in FIG. 1 (wired system) or FIG. 9 (wireless system), is attached to the permeable region (107) of skin so that semi-permeable membrane (not shown in FIG. 1) is in contact with the permeable skin. When a wireless TAMS is used, typically, the hydrogel and sensor are placed in the target plate and aligned with the center hole (125). Then the sensor housing (126) is attached and connected to the target plate (120) to form the complete sensor assembly (112).

An analyte may be extracted through the treated, permeable region (107) of the user's skin, and pass through the semi-permeable membrane so that it is in contact with the hydrogel disc (106) of the sensor body (101).

For example, an analyte, such as glucose, may be transported by diffusion through the semi-permeable membrane and into the hydrogel disc (106) where it can contact glucose oxidase. The glucose then reacts with the glucose oxidase present in the hydrogel disc (106) to form gluconic acid and hydrogen peroxide. Next, the hydrogen peroxide is transported to the surface of the electrode in the sensor body (101) where it is electrochemically oxidized. The current produced in this oxidation is indicative of the rate of hydrogen peroxide being produced in the hydrogel, which is related to the amount of glucose flux through the skin (the rate of glucose flow through a fixed area of the skin). The glucose flux through the skin is proportional to the concentration of glucose in the blood of the user.

The signal from the sensor assembly can thus be utilized to continuously monitor the blood glucose concentration of a user by displaying blood glucose concentration on the potentiostat recorder (108) in a continuous, real-time manner.

In principle, any sensor which utilizes the working electrode (201), the counter electrode (202) and the reference electrode (203) to measure hydrogen peroxide can be built in the same way. Examples are biosensors for glucose, lactate or any others using oxidase enzyme incorporated in the hydrogel (106). The electrochemical sensor is preferably operated in potentiostat mode during continuous glucose monitoring. In potentiostat mode, the electrical potential between the working and reference electrodes of a three-electrode cell are maintained at a preset value. The current between the working electrode and the counter electrode is measured. The sensor is maintained in this mode as long as the needed cell voltage and current do not exceed the current and voltage limits of the potentiostat. In the potentiostat mode of operation, the potential between the working and reference electrode may be selected to achieve selective electrochemical measurement of a particular analyte or analyte indicator.

Other operational modes can be used to investigate the kinetics and mechanism of the electrode reaction occurring on the working electrode surface, or in electroanalytical applications. For instance, according to an electrochemical cell mode of operation, a current may flow between the working and counter electrodes while the potential of the working electrode is measured against the reference electrode. It will be appreciated by those skilled in the art that the mode of operation of the electrochemical sensor may be selected depending on the application.

EXAMPLES

Example 1

The Use of a Protective Semi-Permeable Membrane to Form a Hydrogel/Membrane Composite, and Improve TAMS Performance The following membranes were tested: [a] Uncoated Polyether sulphone (PES): symmetric with pore sizes of 0.2, 1.2 and 5.0 µm; asymmetric with pore sizes of 0.3, 1.0 and 2.0

μm, [b] Nafion®-coated PES: each of the 6 different PES pore sizes listed above were also tested with a Nafion® coating, [c] Activated PES with aldehyde functional groups (with pores of 0.45 μm), [4] Amphoteric and cationic Nylon 66 (with pores of 0.2 μm), [d] Ultrafiltration membranes: Regenerated Cellulose (RC) with 3.5 k MW cutoff; PES with 10 k MW cutoff [e] Nafion 1135 sheet, with ~35 nm ionic channels.

Formation of a hydrogel/membrane composite: the membrane was cut out as a disc, soaked in buffer and placed at the bottom of the polymerization mold; the scrim page was placed over the membrane; polymer solution was syringed into the mold cavity; the mold was exposed to UV light to form the polymer.

For membranes formed from Nafion®-coated PBS, the PES membrane was pre-coated with a Nafion® solution using an automated coating machine. The coating parameters included machine speed, coating bar size, Nafion® solvent, and number of coats, and varied with the pore size of the PES. The coating parameters affect the thickness of the coat, how deep it sinks into the membrane, its consistency, and its longevity. For example, a light surface coating resulted when 0.2 μm PES was singly coated with 5% Nafion® solution (in 45% alcohol) at 8 inches/sec using a #20 bar; a deeper coat resulted with multiple coatings of 5.0 μm PES with 20% Nafion® solution (in 80% alcohol) using a #20 bar. The depth of the Nafion® coating was determined by dying the coated membrane with cationic methylene blue.

Where the pore size of the membrane was smaller than the 3.4 k PEG macromer (as with 3 k cellulose), a smaller 0.75 k PEG macromer was used to connect the membrane to the 3.4 k PEG network. In this case, when the PEG macromer (at 3.4 k Daltons) could not penetrate the pores of the membrane (at 3 k Daltons), a 0.75 k PEG macromer was used to form two interconnecting IPNs. The 0.75 PEG macromer was first polymerized within one face of the 3 k membrane; subsequently, the 3.4 k PEG macromer was polymerized at the new membrane face that now presented a 0.75 k PEG network.

24-hr ex vivo studies were run to study the effect of each membrane on the glucose sensor's performance. Subject groups that had either no membrane or various types of membranes were compared. The membrane that increased the longevity of the device, without increasing MARD error, was determined to be the preferred membrane. Each membrane was applied to the outer surface of the sensor assembly in a CGM device (supplied by Sontra Medical), which was then applied over the sonicated skin of the subject. In response, the device provided an electrical signal, in nanoamperes (nA), which was calibrated to the blood glucose (BG) of the subject, using a finger-stick blood glucose meter. Throughout the course of the ex vivo study (24 hours in length), finger-stick BG samples were taken during the waking hours, at hourly intervals, or at 15-minute intervals near meal times, and were correlated to the signal of the device. Analysis of this correlation provides information about device accuracy, consistency and effective length of performance.

Figure 3:
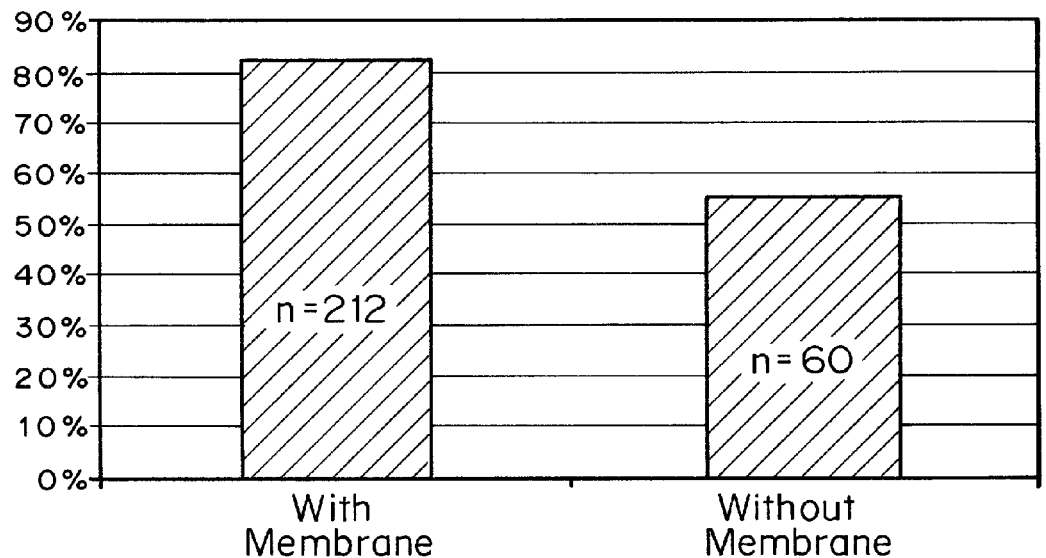
FIG. 3 is a bar graph of the percentage of the remaining signal from the exemplary biosensor with and without barrier membranes after 24-hr of ex vivo applications, where "n" represents the number of tests.

In general, the addition of any membrane to the hydrogel prolonged the use life of the glucose sensor. As shown in FIG. 3, in ex vivo applications without membranes, only 55% of the subjects had any 24-hr response; with the membrane, 83% of the subjects had a 24-hr response (see FIG. 3).

Figure 4:
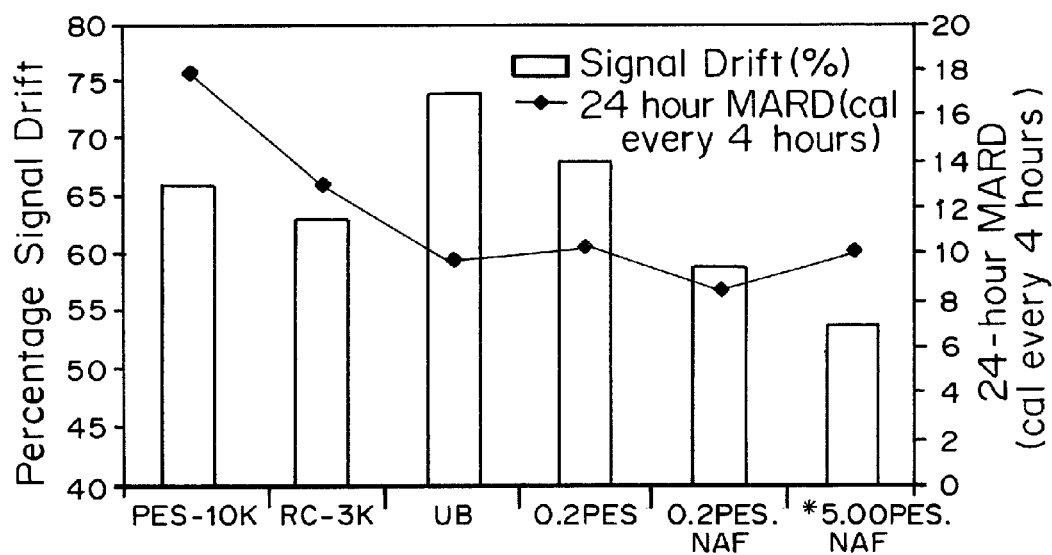
FIG. 4 shows a bar graph of signal drift (%) and 24-hr Mean Absolute Relative Difference (MARD) between the sensor (nA) and blood glucose (BG) levels for the device with different membranes, calibrated every 4 hours. The labels "PES-10K" (Poly(ether sulfone)) and "RC-3k" refer to UF membranes, "UB" refers to covalently activated PES, "0.2PES" refers to uncoated with 0.2 µm pores, ".NAF" refers to Nafion®-coated, and the asterisk (*) indicates that for this sensor, MARD is quoted with calibration every 8 hours.

There was a difference among membranes, and the criteria used to select the best membrane was the one with the lowest signal drift over 24 hours, while still providing good signal correlation (in nA to BG) (i.e. no significant increase in MARD error). A Nafion® coated PES membrane with 5.0 μm pores was determined to be the best candidate because it demonstrated the lowest signal drift of ~54% over 24 hrs, and acceptable MARD (see FIG. 4).

Example 2

The Inclusion of a Humectant in the Hydrogel Buffer to Mitigate Water Loss, and to Improve Device Performance A series of experiments was conducted including various humectants in the hydrogel. Two categories of humectants were tested. The first category contained small-molecule humectants, generally natural moisturizing factors (NMFs), and the second category contained polysaccharides. The following small-molecule humectants were tested: glycerol, urea, hydroxyethyl urea, propylene glycol, sodium lactate (Na lactate) and sodium pyrrolidone carboxylic acid (Na PCA). The following polysaccharide humectants were tested: hyaluronic acid (sodium salt), carrageenan and agarose.

For the small-molecule humectants, each humectant was dissolved in the polymer solution before polymerization. The particular concentration of humectant in the polymer solution was also maintained in the hydrogel buffer. This prevented a humectant concentration gradient that could promote humectant diffusion loss during rinsing and storage.

For the polysaccharide humectants, the same general approach was used as described above for small-molecule humectants. However, certain candidates such as agarose and isolated carrageenan types needed heating for proper solubility, and cooling for gel formation. The PEGDA concentration was dropped to 10% to increase the polysaccharide solubility.

Screening experiments were first performed to select the best candidates for limited ex vivo experiments. Screening experiments involved solubility and drying rate comparisons.

24-hr ex vivo studies were run to study the effect of each humectant on the glucose sensor's performance. Subject groups that had either no humectant or various types of humectants were compared. The humectant that increased the longevity of the device, without increasing MARD error, was determined to be the preferred humectant. The ex vivo experiments involved the application of the device to volunteers for 24 hrs, and then comparing the longevity performance when different humectants were included Similar to the Example 1, the goal of humectant inclusion study was to prolong the device performance. The results of the test are provided in FIG. 5. While many of the humectants showed some promise, including sodium lactate, carrageenan, and agarose, Na PCA consistently provided the lowest signal drift (see FIG. 5). Also, when Na PCA was paired with Nafion®-coated PES membranes, there was no water loss over the course of the 24-hr ex vivo studies. Data collected from 27 subjects show an actual water gain of 2%. However, typically, there was a water loss for 24-hr studies. In a comparable group of 36 subjects without Na PCA in the study, an average water loss of 19% was observed.

Example 3

Covalent Immobilization of Glucose Oxidase (GOx) within a PEGDA Hydrogel

A series of experiments was conducted to establish a practical enzyme immobilization strategy. An acrylate-PEG-NHS (A-PEG-N) reagent (Nektar) was chosen as the linker or immobilization reagent. Parameters of concern included the ratio of immobilization reagent to enzyme, reaction sequence, and incubation time.

A pre-polymerization step for incubation of the acrylate-PEG-NHS (A-PEG-N) immobilization reagent to the enzyme was used. 3% GOx was dissolved in the polymerization buffer, and an excess of A-PEG-N at a molar ratio of 7 to 1 was added. A molar ratio of 7 to 1 was chosen to ensure conjugation, without interfering with enzyme activity. The solution was left to incubate overnight at 4° C. (a reaction time of 3 hours at room temperature was also effective). PEGDA was added per usual the next day to complete the polymer solution, followed by UV curing.

Evidence that the covalent immobilization was successful was provided by 10% PEGDA polymers containing 3% GOx. Without covalent immobilization, the GOx leached out of a hydrogel disc when placed in a rinse buffer solution, and turn the solution distinctly yellow (UV absorbance at 460 nm=0.16). With covalent immobilization, the rinse solution did not turn yellow (UV absorbance at 460 nm=0.02).

Evidence that the enzyme was still active after covalent immobilization was provided by potentiostat testing, which showed no significant differences in responses to a glucose challenge: ~700 nA for the control system, and ~650 nA for the covalently immobilized system.

After the covalent immobilization parameters were established, ex vivo experiments were conducted to determine if the consistency of the readings by the system had been improved. The ex vivo experiments involved the application of the device to volunteers for 4 hrs, and then comparing the performance to a device without covalent immobilization, by performing statistical analysis and calculating the $r^2$ and MARD values.

Figure 6:
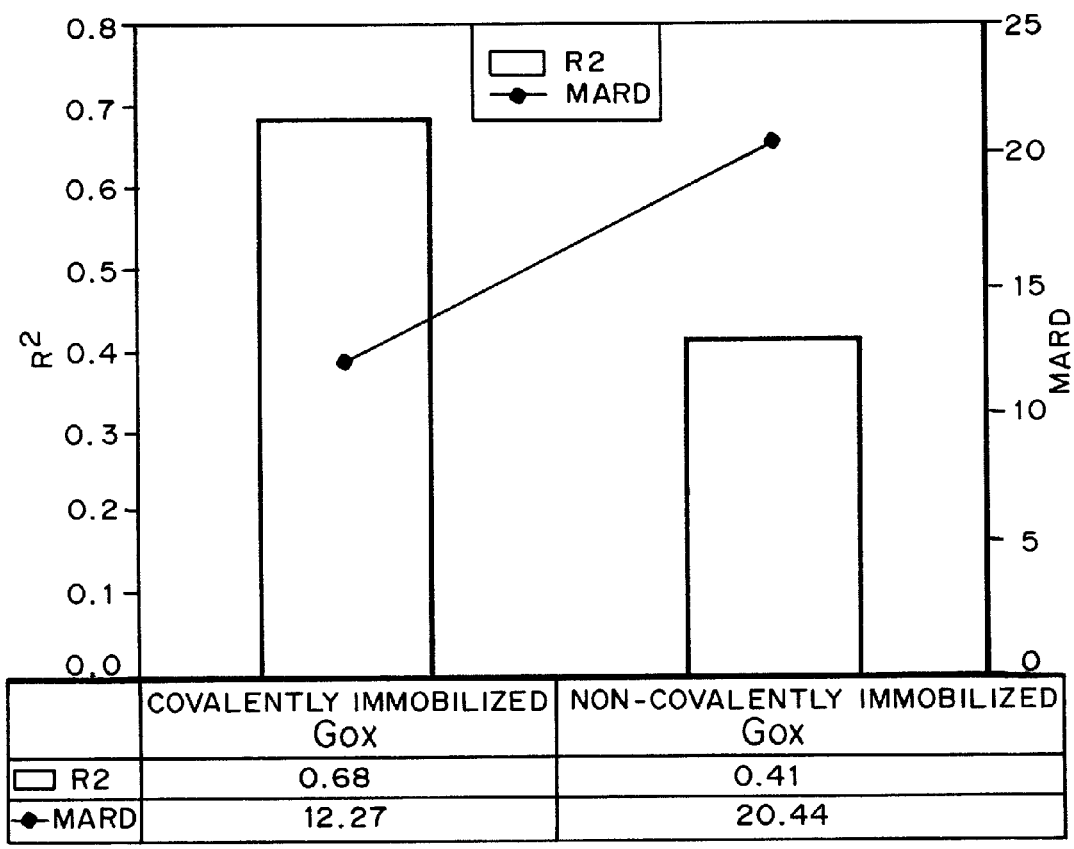
FIG. 6 shows a bar graph comparing a biosensor system with covalently immobilized COx to one without covalent immobilization, using nA to BG correlation ($R^2$) and MARD, after 4-hour ex vivo application.

In a 4-hr comparative study of ex vivo device performance for covalently immobilized GOx vs. non-covalently immobilized GOx, the covalently immobilized GOx system provided better tracking (nA to BG correlation). The results of this study are shown in FIG. 6. As shown in FIG. 6, after the adoption of the covalently immobilized GOx, ex vivo studies provided more consistent tracking, with an $r^2$ of 0.68, and an MARD of 12.27. In contrast, for the system with non-covalently immobilized GOx, the $r^2$ value was 0.41, and the MARD was 20.44.

Example 4

Skin Preparation Procedure for Transdermal Analyte Detection

A target plate was first applied to the skin. Then, SonoPrep® was applied to the skin site through the target plate. SonoPrep® was then turned on for a period of one second or longer and shut off automatically by the build-in control algorithm of the device. After the skin pretreatment procedure by applying SonoPrep® (Sontra Medical) to increase porosity of the skin, the treated skin site was wiped with a skin preparation wipe. The skin preparation wipe used in this study was gauze pad pre-soaked in 70%/30% of isopropanol/water mixture.

Figure 7A:
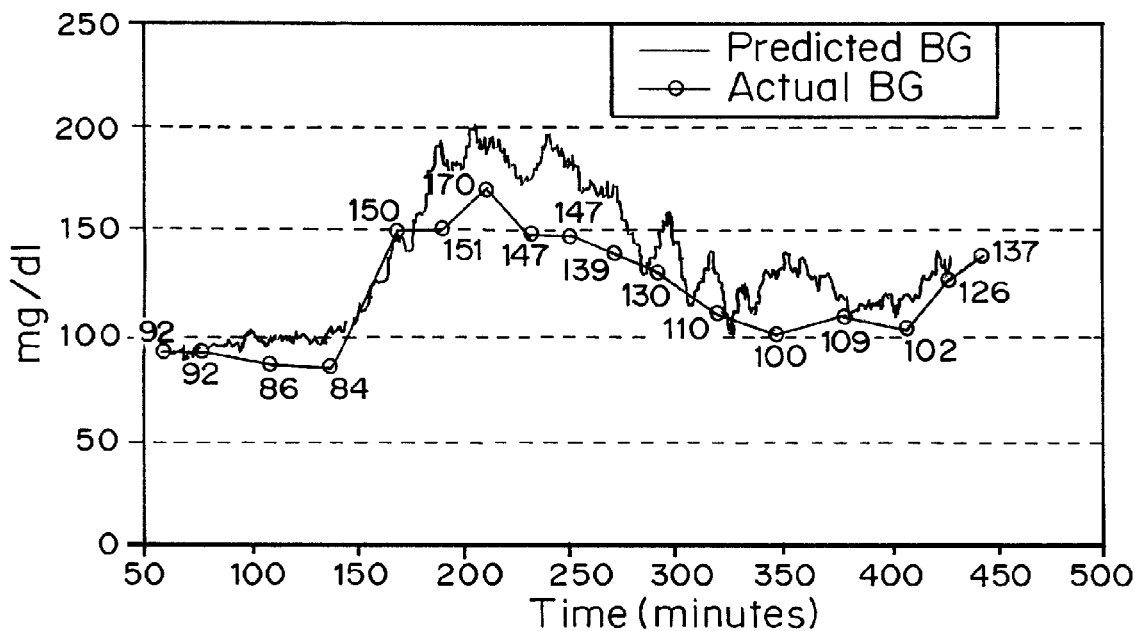
FIG. 7A is a line graph of blood glucose concentrations (mg/dl) versus time (minutes) taken from a continuous, transdermal glucose sensor with a skin preparation wiping procedure performed prior to applying the sensor. Reference blood glucose ("Actual BG", finger stick blood glucose meter reading, solid line with circles) levels are compared to predicted blood glucose ("Predicted BG", the sensor's glucose reading, solid line) levels. The data shows a strong correlation (r=0.950) between the Predicted BG and the Actual BG.
Figure 7B:
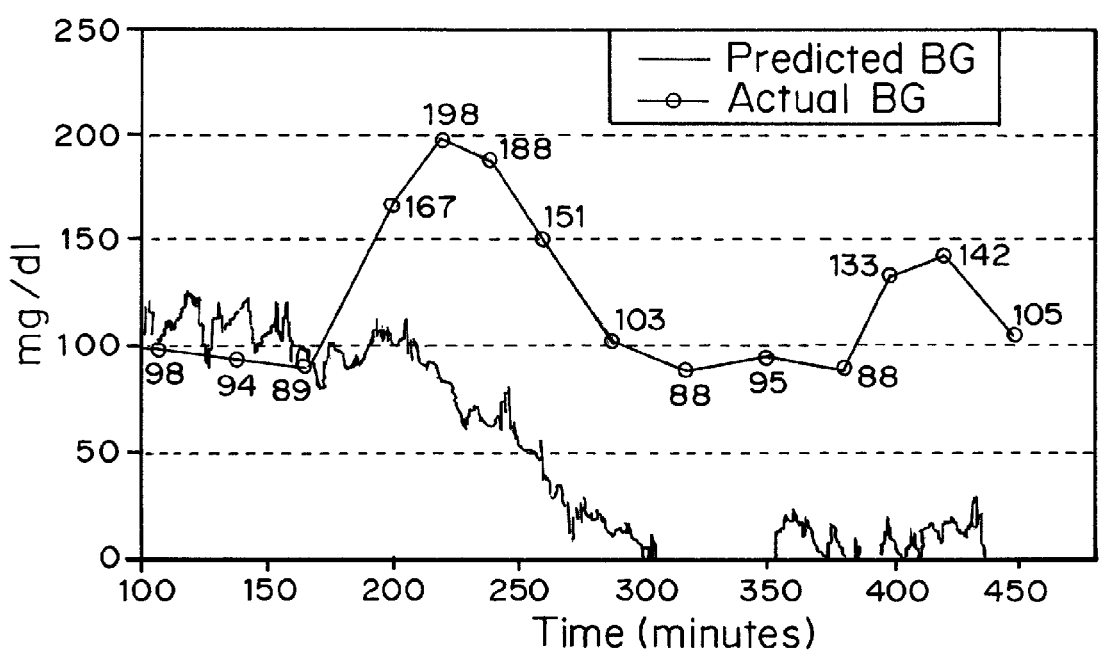
FIG. 7B is a line graph of blood glucose concentrations (mg/dl) versus time (minutes) taken from a continuous, transdermal glucose sensor without any skin preparation procedure prior to applying the sensor. Reference blood glucose ("Actual BG", finger stick blood glucose meter reading, solid line with circles) levels are compared to predicted blood glucose ("Predicted BG", the sensor's glucose reading, solid line) levels. The data shows a poor correlation (r=0.309) between the Predicted BG and the Actual BG.
Figure 7C:
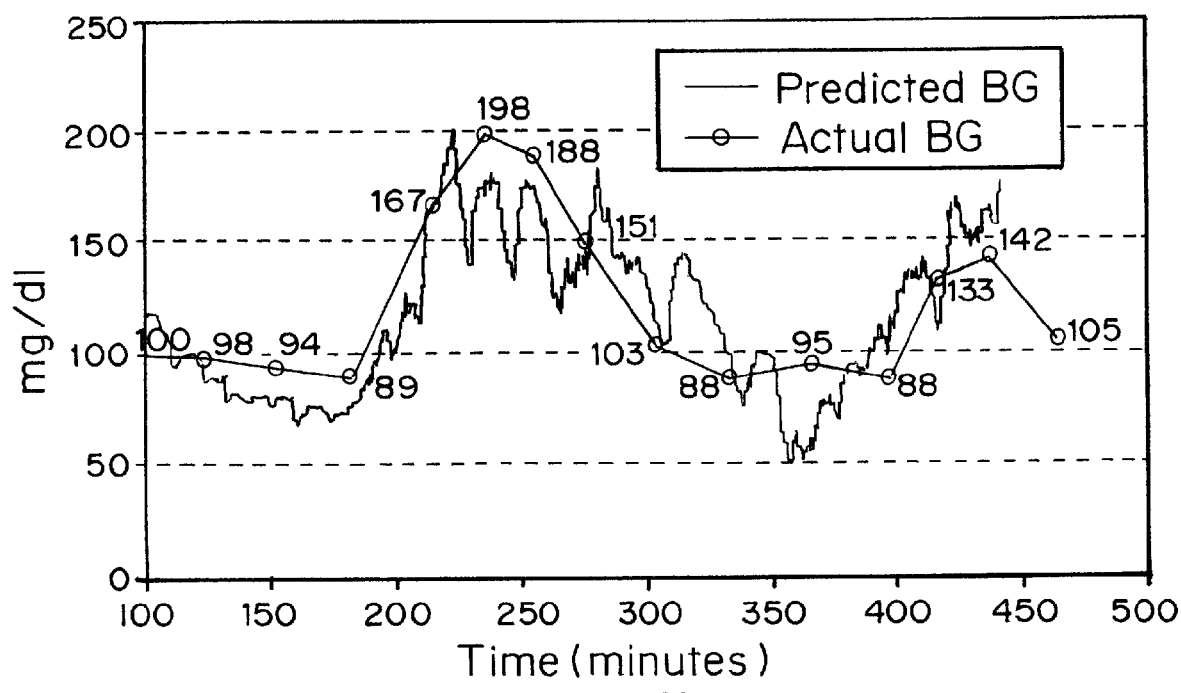
FIG. 7C is a line graph of blood glucose concentrations (mg/dl) versus time (minutes) taken from a continuous, transdermal glucose sensor with a 40-minute skin hydration procedure performed prior to applying the sensor. Reference blood glucose ("Actual BG", finger stick blood glucose meter reading, solid line with circles) levels are compared to predicted blood glucose ("Predicted BG", the sensor's glucose reading, solid line) levels. The data shows a strong correlation (r=0.947) between the Predicted BG and the Actual BG.

FIGS. 7A and 7B demonstrate the difference in sensor performance with and without applying a skin preparation wiping procedure on one test subject. As a contrast to the skin preparation wipe procedure, FIG. 7C shows the result of the same test subject when a 40-minute hydration procedure (i.e. prior art procedure) was used. As shown in the figures, wiping the treated skin with the skin preparation wipe shows equivalent performance to 40-minutes skin hydration procedure, and both of these methods perform much better than that without any skin preparation procedure. Removal and/or cleaning of any pore clogging materials by skin preparation wipe is expected to improve transdermal pathways for both analyte extraction and drug delivery.

Example 5

Clinical Studies with Continuous Transdermal Glucose Sensor with Three Different Configurations The glucose biosensor contains an electrochemical sensor and a hydrogel that couple with SonoPrep® ultrasonic permeated skin and continuously draws the glucose into the sensor. The glucose that flows through the skin is consumed by the biosensor as it reacts with glucose oxidase in the hydrogel. This chemical reaction produces a constant electrical signal, which is recorded by the glucose monitor. Due to the enhanced permeation created by SonoPrep and the hydrogel chemistry, the glucose flux detected by the sensor can provide glucose readings through a wireless link every one minute for up to 24 hours. See FIG. 9 for schematics of the wireless biosensor system.

In each study, the following procedure was used. This procedure is schematically illustrated in FIG. 9. First, the target plate was placed on the patient's skin site. Then SonoPrep was applied to the skin site for 5 to 15 seconds (step 1). Then SonoPrep was removed from the target plate. Then the treated skin site was wiped with a skin preparation wipe containing alcohol. Next, the hydrogel and sensor was placed in the target plate (step 2). For each patient, single-use glucose sensors were placed over the SonoPrep treated skin sites. Then the sensor housing was placed over the hydrogel and the sensor assembly was closed (step 3). The sensor was coupled with a miniature analyzer which sent digitized data wirelessly to a monitor for data processing and display (step 3). The glucose sensor signal was referenced to finger stick blood glucose meter readings for Study 1A and Study 1B and to blood glucose was sampled through an IV line for Study 2C.

Table 1 describes the sensor configurations, type of membrane used (if a membrane was present), and type of humectant included in the hydrogel (if a humectant was present) for each of the studies. The sensors used in each of the studies were designed to provide enhanced oxygenation (such as illustrated in FIGS. 8A, 8B, and 8C). Additionally, the hydrogels used in each of the studies contained 3% GOx covalently immobilized in 15% PEGDA.

TABLE 1

Sensor configurations, materials and duration for Each Study

| Study # | Sensor configuration | Duration | Membrane | Humectant |
|---|---|---|---|---|
| 1 | A | 12 h | N/A | N/A |
| 1 | B | 12 h | Biodyne B | N/A |
| 2 | C | 24 h | 5.0 PES•NAF | 10% NaPCA |

Study 1 with Sensor Configuration A 10 patients with diabetes were tested using the method described above. As noted in Table 1, this study was conducted for 12 hours. The sensor used in this study did not have a membrane over the hydrogel. Additionally, the hydrogel did not contain a humectant.

Figure 10:
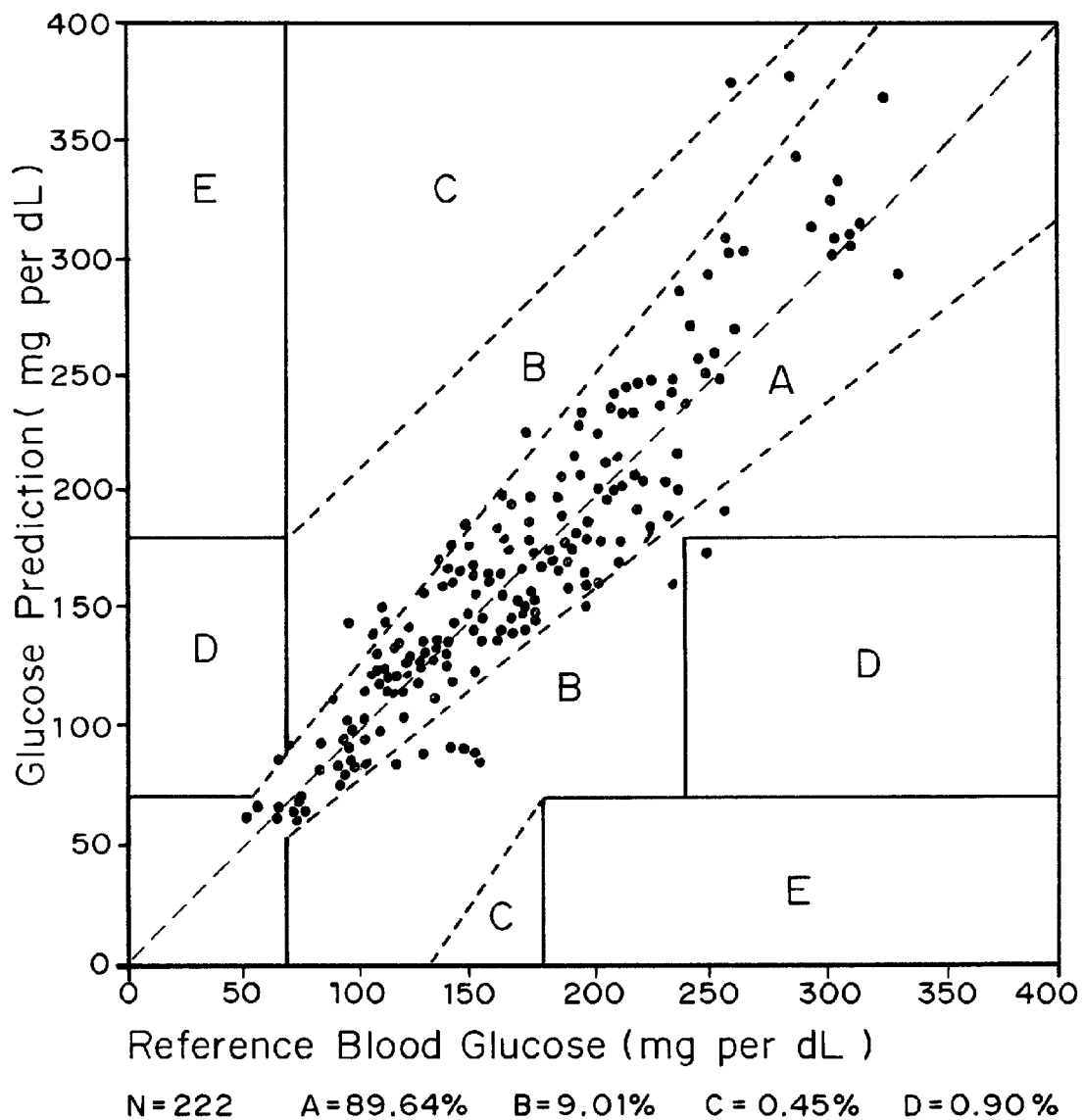
FIG. 10 is a Clarke error grid of the data obtained in Study 1A, with 222 sensor-blood glucose data points collected from 10 patients.

222 data points from this study were analyzed to support development of the blood glucose prediction algorithm. The results are summarized in the Clarke error grid in FIG. 10. As shown in FIG. 10, the results showed that the sensor could accurately predict blood glucose reading every minute for up to 12 hours with single point calibration after one hour of warm-up period.

Comparing the biosensor and reference blood glucose measurements, statistical analysis showed the MARD (Mean Absolute Relative Difference) was 12.4%. 98.7% of the data fell in the A+B region of the Clarke error grid with 89.6% in the A region. Excellent data correlation (average r=0.87) was again demonstrated with this study (see FIG. 10). These statistics are summarized in Table 2, along with the statistics for the other studies described in this Example.

Study 1 with Sensor Configuration B

The same study protocol and configuration as in Study 1A were used, except that a filter membrane (Biodyne B) was incorporated with the hydrogel 10 patients with diabetes were tested using the method described above. As noted in Table 1, this study was conducted for 12 hours. The sensor used in this study had a membrane (Biodyne B) over the hydrogel. Additionally, the hydrogel did not contain a humectant.

Figure 11:
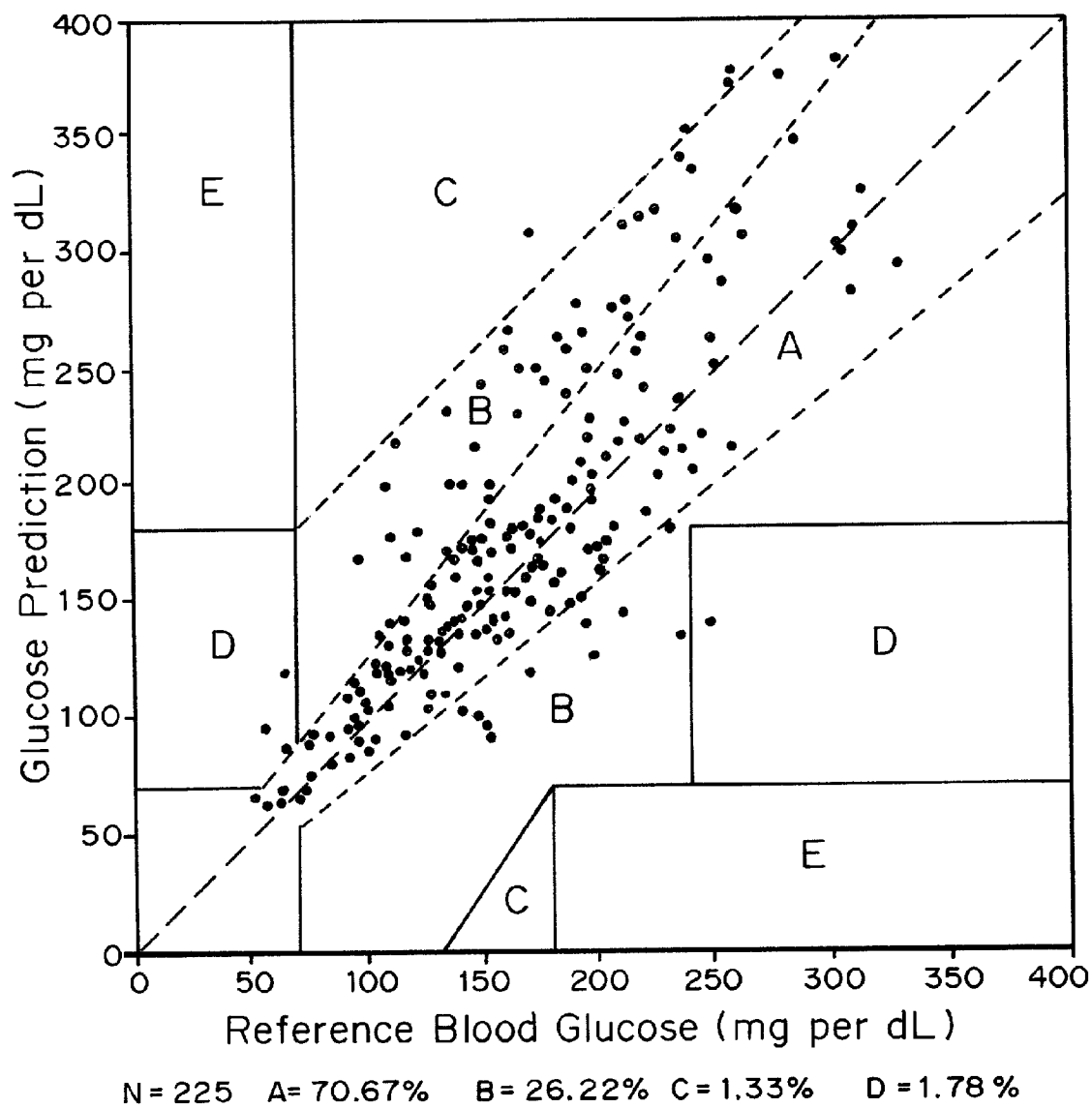
FIG. 11 is a Clarke error grid of the data obtained in Study 1B, with 225 sensor-blood glucose data points collected from 10 patients.

225 data points were collected from this study. The results are summarized in the Clarke error grid in FIG. 11. As shown in FIG. 11, the results showed that the sensor could predict blood glucose reading with moderate accuracy, every minute for up to 12 hours with single point calibration after one hour of warm-up period.

Comparing the biosensor and reference blood glucose measurements, statistical analysis showed the MARD (Mean Absolute Relative Difference) was 20.4%. 96.9% of the data fell in the A+B region of the Clarke error grid with 70.7% in the A region. The correlation coefficient between the biosensor and reference blood glucose measurements was 0.64. These statistics are summarized in Table 2, along with the statistics for the other studies described in this Example.

Study 2 with Sensor Configuration C

A 24-hour clinical study was conducted on patients during and after cardiovascular surgery. As noted in Table 1, the sensor used in this study had a membrane (5.0 PES coated with NAFION®) over the hydrogel. Additionally, the hydrogel contained a humectant (10% (wt/wt) Na PCA).

During the surgery, the patient's core temperature was brought down to about 20° C. and the patient's heart was put into stop with the aid of a bypass pump for blood circulation. Medication such as insulin and heparin were administered and blood glucose was sampled through an IV line and analyzed with a blood glucose analyzer.

In the first section of the study, it was determined that moisture and betadine (a disinfectant used to prepare the skin prior to surgery) adversely affected the sensor and resulted in device failure. Temporary modifications to the device configuration and installation procedure (e.g. avoid skin area with betadine) were then implemented to address those issues.

In the second section of the study after the device modification, 10 patients enrolled and nine completed the study. 147 sensor-blood glucose data points were collected and analyzed with the same glucose prediction algorithm developed in Study 1A.

Figure 12:
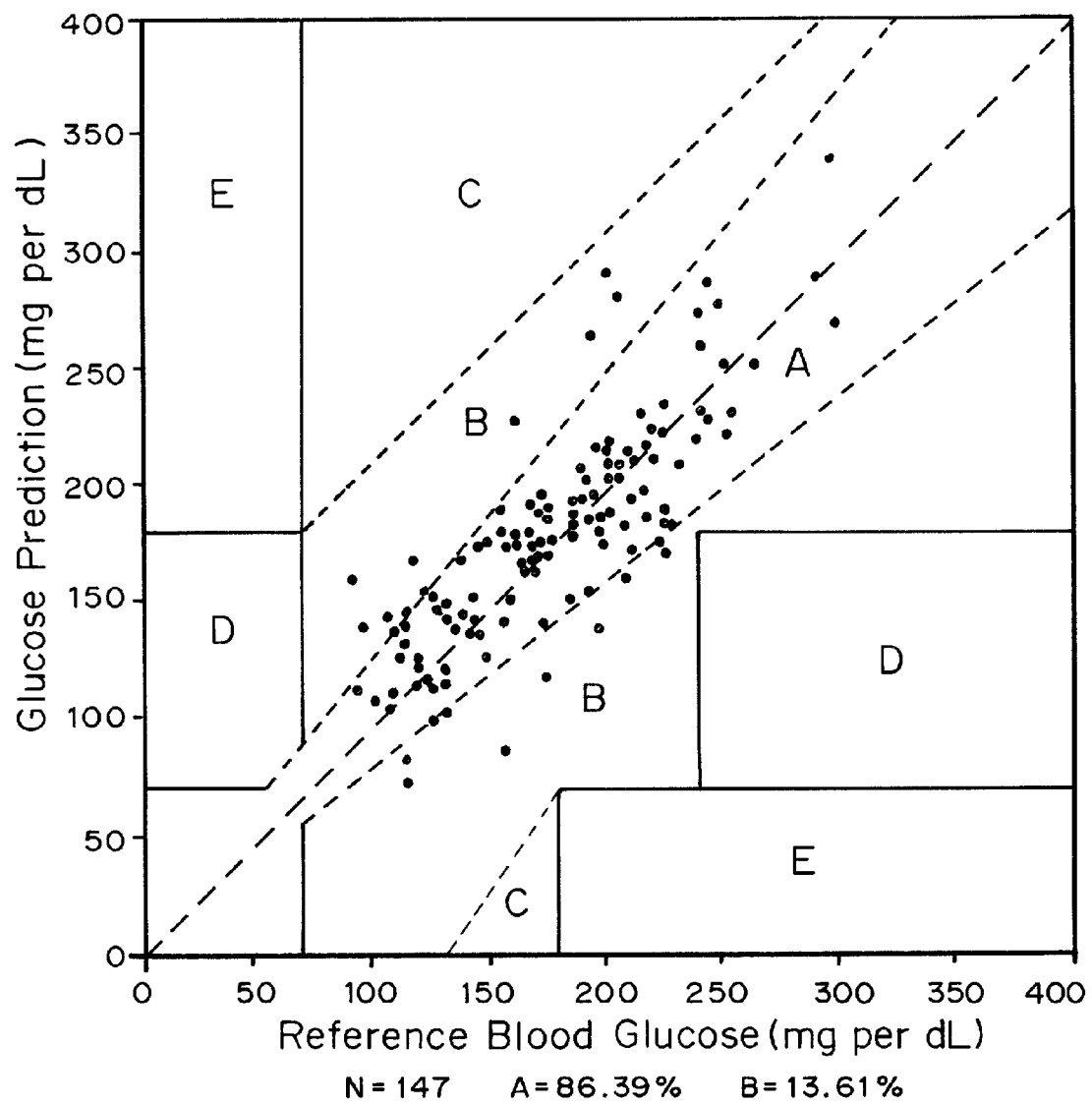
FIG. 12 is a Clarke error grid of the data obtained in Study 2C, with 147 sensor-blood glucose data points collected from 10 patients (9 of whom completed the study).

The results are summarized in the Clarke error grid in FIG. 12. As shown in FIG. 12, the results showed that the sensor could accurately predict blood glucose reading every minute for up to 24 hours, during and post operation.

Comparing the biosensor and reference blood glucose measurements, statistical analysis showed the MARD was 11.2%, and 100% of the data fell in the A+B region of the Clarke error grid with 86.4% in the A region. This study illustrates that with proper device configuration and installation a transdermal glucose monitor can also provide accurate continuous glucose reading for up to 24 hours, even in a surgical ICU setting.

TABLE 2

Summary table for Statistical Analysis in Clinical Studies

| Study # | Setting | # of Subj. | Device config. | # of calibration | (A + B)% in CEG | MARD | R2 |
|---|---|---|---|---|---|---|---|
| 1 | Diabetes 12 h | 9/10 | A | 1 | 98.7 | 12.4% | 0.77 |
|  |  |  | B | 1 | 96.9 | 20.4% | 0.64 |
| 2 | Surgical ICU, 24 h | 9/36 | C | 2-3 | 100 | 11.2% | 0.83 |

Those skilled in the art will recognize, or be able to ascertain using no more than routine experimentation, many equivalents to the specific embodiments of the invention described herein. Such equivalents are intended to be encompassed by the following claims.

We claim:

1. A transdermal analyte monitoring system comprising:
a sensor assembly, wherein the sensor assembly comprises a hydrogel and a sensor body containing a plurality of electrodes, wherein the sensor body is in fluid communication with the hydrogel, wherein the hydrogel comprises a humectant and an enzyme, and wherein the humectant is in an effective amount to increase the performance longevity of the transdermal analyte monitoring system, as indicated by decreased signal drift, compared to the same system in the absence of the humectant, and
wherein the humectant is sodium pyrrolidone carboxylic acid (NaPCA).

2. The transdermal analyte monitoring system of claim 1, wherein the hydrogel comprises a polymer selected from the group consisting of polyethylene glycol diacrylate (PEGDA), agarose, polyethylene glycol diacrylate/polyethyleneimine (PEGDA-PEI), polyethylene glycol diacrylate-n-vinyl pyrrolidone (PEGDA-NVP), acrylate-polyethylene glycol-N-hydroxy succinimide (A-PEG-N), and blends and copolymers thereof.

3. The transdermal analyte monitoring system of claim 1, wherein the enzyme is oxidase enzyme.

4. The transdermal analyte monitoring system of claim 1, wherein the enzyme is covalently immobilized in the hydrogel.

5. The transdermal analyte monitoring system of claim 4, wherein the enzyme is covalently immobilized in the hydrogel using an A-PEG-N.

6. The transdermal analyte monitoring system of claim 1, wherein the sensor assembly comprises at least one channel or pocket for providing oxygen to the hydrogel.

7. The transdermal analyte monitoring system of claim 1, wherein the enzyme is immobilized in the hydrogel via non-covalent immobilization.

8. The transdermal analyte monitoring system of claim 1, further comprising a semi-permeable membrane on the surface of the hydrogel, wherein the membrane is in fluid communication with the hydrogel.

9. The transdermal analyte monitoring system of claim 8, wherein the hydrogel and the semi-permeable membrane form an interpenetrating polymer network.

10. A method for increasing analyte detection by a transdermal analyte monitoring system comprising:
(a) treating a region of skin of the user to increase permeability; and
(b) applying to the treated region of skin a transdermal analyte monitoring system comprising
a sensor assembly, wherein the sensor assembly comprises a hydrogel and a sensor body containing a plurality of electrodes, wherein the sensor body is in fluid communication with the hydrogel wherein the hydrogel comprises a humectant and an enzyme, and wherein the humectant is in an effective amount to increase the performance longevity of the transdermal analyte monitoring system, as indicated by decreased signal drift, compared to the same system in the absence of the humectant, and
wherein the humectant is sodium pyrrolidone carboxylic acid (NaPCA).

11. The method of claim 10, wherein the region of skin is treated in step (a) by a method selected from the group consisting of tape stripping, rubbing, sanding, abrasion, laser ablation, radio frequency (RF) ablation, the application of chemicals, sonophoresis, iontophoresis, electroporation, and the application of permeation enhancing agents.

12. The method of claim 10, further comprising providing an enhanced supply of oxygen to the hydrogel.

13. The method of claim 12, wherein the source of oxygen is air.

14. The method of claim 12, wherein the enzyme in the hydrogel is an oxidase enzyme.

15. The method of claim 10, further comprising after step (a) and prior to step (b), wiping the treated region of skin with a substrate comprising at least one reagent selected from the group consisting of water, ethanol, isopropanol and glycerol.

16. The method of claim 10, wherein the analyte to be detected is blood glucose, lactate or other analytes.

* * * * *